(12) United States Patent
Peot et al.

(10) Patent No.: US 8,758,018 B2
(45) Date of Patent: Jun. 24, 2014

(54) EEG-BASED ACCELERATION OF SECOND LANGUAGE LEARNING

(75) Inventors: Mark Peot, Chapel Hill, NC (US); Mario Aguilar, Jacksonville, AL (US); Aaron T. Hawkins, Raleigh, NC (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 1075 days.

(21) Appl. No.: 12/650,734

(22) Filed: Dec. 31, 2009

(65) Prior Publication Data

US 2011/0159467 A1 Jun. 30, 2011

(51) Int. Cl.
*G09B 17/00* (2006.01)
*G09B 19/08* (2006.01)
*G09B 5/02* (2006.01)

(52) U.S. Cl.
USPC ............ 434/157; 434/156; 434/167; 434/178

(58) Field of Classification Search
USPC .................................................. 434/157, 178
See application file for complete search history.

(56) References Cited

U.S. PATENT DOCUMENTS

| | | | |
|---|---|---|---|
| 4,034,401 A | 7/1977 | Mann | |
| 4,287,809 A | 9/1981 | Egli | |
| 4,332,566 A * | 6/1982 | Mazeski et al. ............... | 434/178 |
| 4,753,246 A | 6/1988 | Freeman | |
| 5,083,924 A * | 1/1992 | Cochran et al. ............... | 434/178 |
| 5,231,674 A | 7/1993 | Cleveland | |
| 5,513,649 A * | 5/1996 | Gevins et al. ................. | 600/544 |
| 5,583,795 A | 12/1996 | Smyth | |
| 5,617,872 A | 4/1997 | Scinto | |
| 5,632,282 A | 5/1997 | Hay | |
| 5,649,061 A | 7/1997 | Smyth | |
| 5,797,853 A | 8/1998 | Musha | |
| 5,846,208 A * | 12/1998 | Pichlmayr et al. ............ | 600/544 |
| 6,090,051 A * | 7/2000 | Marshall ....................... | 600/558 |
| 6,092,058 A * | 7/2000 | Smyth ............................. | 706/10 |
| 6,102,870 A | 8/2000 | Edwards | |
| 6,230,049 B1 | 5/2001 | Fischell | |
| 6,402,520 B1 * | 6/2002 | Freer ............................. | 434/236 |
| 6,418,424 B1 * | 7/2002 | Hoffberg et al. ................ | 706/21 |
| 6,434,419 B1 * | 8/2002 | Gevins et al. ................. | 600/544 |
| 6,572,562 B2 | 6/2003 | Marshall | |
| 6,931,274 B2 | 8/2005 | Williams | |
| 7,202,809 B1 | 4/2007 | Schade | |
| 7,231,245 B2 | 6/2007 | Greenwald | |
| 7,257,439 B2 | 8/2007 | Llinas | |
| 7,344,251 B2 * | 3/2008 | Marshall ....................... | 351/246 |

(Continued)

OTHER PUBLICATIONS

Reichle et al., "E-Z Reader: A cognitive-control, serial-attention model of eye-movement behavior during reading," Cognitive Systems Research 7 (2006), pp. 4-22.

(Continued)

*Primary Examiner* — Nikolai A Gishnock
(74) *Attorney, Agent, or Firm* — Eric A. Gifford

(57) ABSTRACT

EEG-based acceleration of second language learning is accomplished by measuring via single-trial EEG a learner's cognitive response to the presentation (visual or auditory) of language learning materials and updating a user model of latent traits related to language-learning skills in accordance with the cognitive response. The user model is suitably updated with each trial, each trial being triggered by learner fixation on a portion of visual materials and/or a next phoneme in auditory materials. Additional discrimination may be achieved through the use of saccades or fixation duration features.

20 Claims, 12 Drawing Sheets

(56) References Cited

U.S. PATENT DOCUMENTS

| | | | |
|---|---|---|---|
| 7,438,418 B2* | 10/2008 | Marshall | 351/246 |
| 7,523,078 B2* | 4/2009 | Peot et al. | 706/12 |
| 7,938,785 B2* | 5/2011 | Aguilar et al. | 600/558 |
| 8,019,703 B2* | 9/2011 | Peot et al. | 706/12 |
| 8,094,122 B2* | 1/2012 | Molander et al. | 345/157 |
| 8,244,475 B2* | 8/2012 | Aguilar et al. | 702/19 |
| 8,265,743 B2* | 9/2012 | Aguilar et al. | 600/544 |
| 2002/0099305 A1 | 7/2002 | Fukushima | |
| 2003/0180696 A1* | 9/2003 | Berger et al. | 434/178 |
| 2006/0029912 A1* | 2/2006 | Kearby et al. | 434/116 |
| 2007/0185697 A1 | 8/2007 | Tan | |
| 2007/0236488 A1 | 10/2007 | Mathan | |
| 2007/0248938 A1* | 10/2007 | Ronald | 434/178 |
| 2008/0188777 A1 | 8/2008 | Bedziouk | |
| 2009/0171240 A1* | 7/2009 | Aguilar et al. | 600/558 |
| 2009/0285500 A1* | 11/2009 | Peot et al. | 382/254 |
| 2010/0003650 A1* | 1/2010 | Sutz | 434/178 |
| 2010/0009325 A1* | 1/2010 | Afanasiev et al. | 434/236 |
| 2010/0185113 A1* | 7/2010 | Peot et al. | 600/544 |
| 2011/0159467 A1* | 6/2011 | Peot et al. | 434/157 |

OTHER PUBLICATIONS

Friederici et al., "Mapping sentence form onto meaning:The syntax-semantic interface," Brainresearch 1146 (2007) pp. 50-58.

Anja Hahne, "What's Different in Second-Language Processing? Evidence from Event-Related Brain Potentials," Journal of Psycholinguistic Research, vol. 30, No. 3, 2001, pp. 251-265.

Heckerman et al., "Causal Independence for Probability Assessment and Inference Using Bayesian Networks," Technical Report MSR-TR-94-08, Microsoft Research Advanced Technology Division, Mar. 1994.

Pierre Comon, "Independent component analysis, A new concept?" Signal Processing 36 (1994) pp. 287-314.

C. Frenck-Mestre, "Eye-movement recording as a tool for studying syntactic processing in a second language: A review of methodologies and experimental findings," Second Language Research: (2005), pp. 1-27.

Rossi et al., "The Impact of Proficiency on Syntactic Second-language Processing of German and Italian: Evidence from Event-related Potentials," Journal of Cognitive Neuroscience 18:12, pp. 2030-2048, (2006).

Adam D. Gerson, Cortically coupled computer vision for rapid image serach, IEEE Trans on Neural Systems and Rehabilitation Engineering, vol. 14, No. 2, pp. 174-179, Jun. 2006.

Simon Thorpe, Speed of processing in the human visual system, Nature, vol. 381, Jun. 6, 1006, pp. 520-522.

Lawrence M. Ward, Synchronous neural oscillations and cognitive processes, Trends in Cognitive Science, vol. 7, No. 12, Dec. 2003, pp. 553-559.

Canan Basar-Eroglu, P300-response: possible psychophysiological correlates in delta and theta frequency channels, A Review, International Journal of Psychophysiology 13, (1992).

W.Klimesh, Induced alpha band power changes in the human EEG and attention, Neuroscience Letters 244, (1998), pp. 73-76.

Eric Granholm, Pupillometric measures of cognitive and emotional processes, Internatinal Journal of Psychophysiology 42 (2004), pp. 1-6.

Lucas C. Parra, Recipes for the linear analysis of EEG, NeuroImage 28 (2005) pp. 326-341.

Marios G. Philiastides, Neural representation of task difficulty and decision making during perceptual categorization: a timing diagram, The Journal of Neuroscience, (Aug. 30, 2006).

Lucas C. Parra, Response error correction—a demonstration of improved human machine performance using real-time EEG monitoring, IEEE Transactions on Neural Systems and Rehabilitation Engineering, vol. XX, No. Y, Month 2003.

German Gomez-Herrero, Automatic removal of ocular artifacts in the EEG without an EOG reference channel, Tampere University of Technology, Finland, (Jun. 7-9, 2006).

Olaf Dimingen, Long reading regressions are accompanied by a P600-like brain potential, Evidence from simultaneous recordings of eye movements and ERPs, Department of Psychology, University of Pottsdam, Germany, (2007).

Olaf Dimingen, Measuring ERP effects of word predictability during left-to-right reading, Department of Psychology, University of Pottsdam, Germany, (2006).

Lucas C. Parra, Single trial detection in EEG and MEG; keeping it linear, Neurocomputing 52-54 (2003) pp. 177-183.

Inhoff et al., Journal of Experimental Psychology: Human Perception and Performance vol. 35(5), Oct. 2009, 1571-1584 (2009).

Ishida et al.,Temporal properties of information extraction in reading studied by a text-mask replacement technique. Josa A, vol. 6, Issue 10, pp. 1624-1632 (1989).

Makeig et al., Independent Component Analysis of Electroencephalographic Data. Advances in Neural Information Processing Systems 8, MIT Press, Cambridge MA, (1996).

Mueller et al., Syntatic learning by mere exposure: An ERP study in adult learners. BMC Neuroscience. Jul. 29, 2009.

Osterhout et al., Novice learners, longitudinal designs, and event-related potentials: A means for exploring the neurocognition of second language processing. Language Learning 2006, 56 (Suppl I): 199-230.

Ikeith Rayner, Eye movements in reading and information processing: 20 years of research. Psychological Bulletin. vol. 124(3), Nov. 1998. 272-422.

Weber et al., Syntatic anomaly elicits a lexico-semantic (N400) ERP effect in the second language but not the first. Psychophysiology 45 (2008).

* cited by examiner

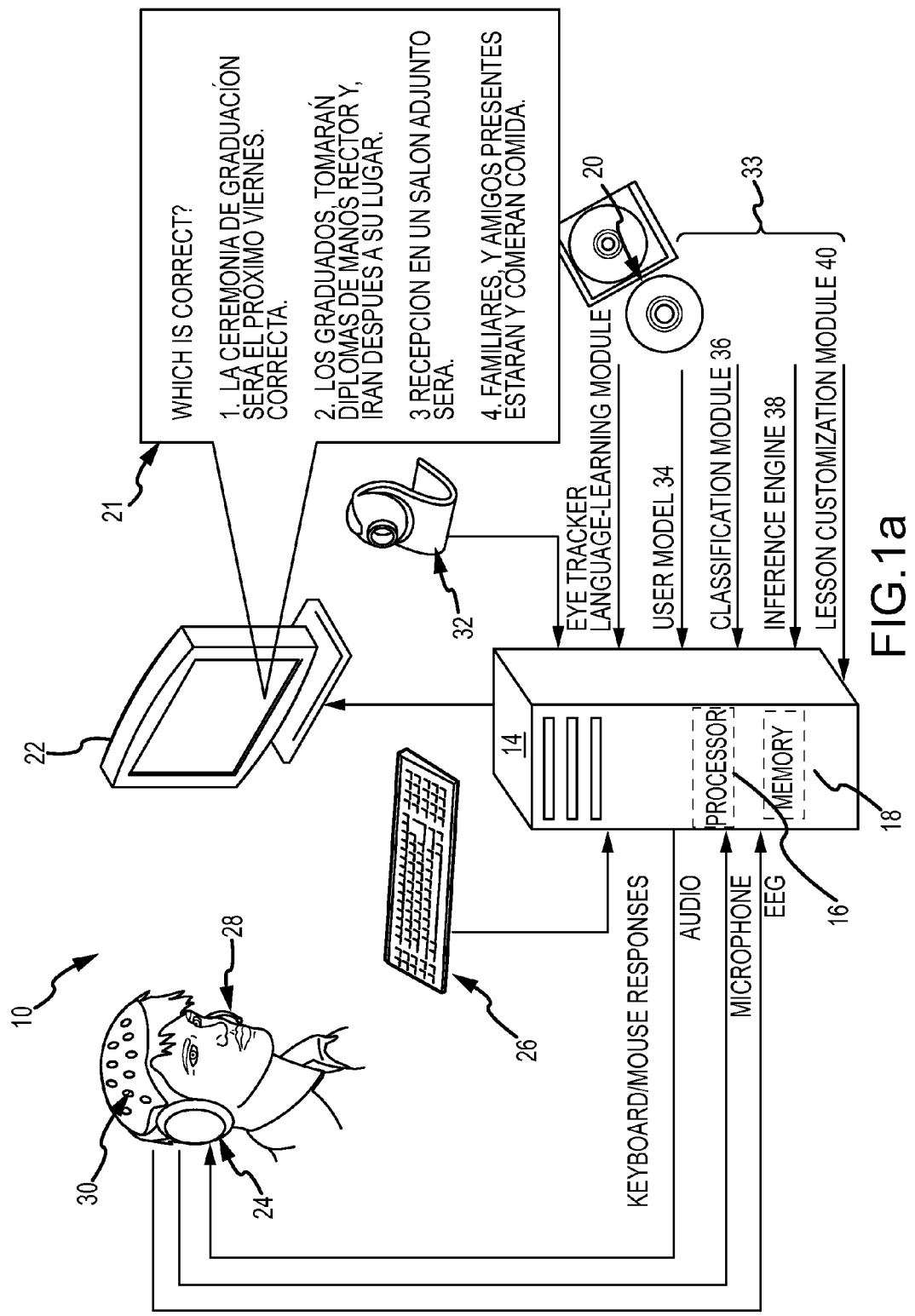

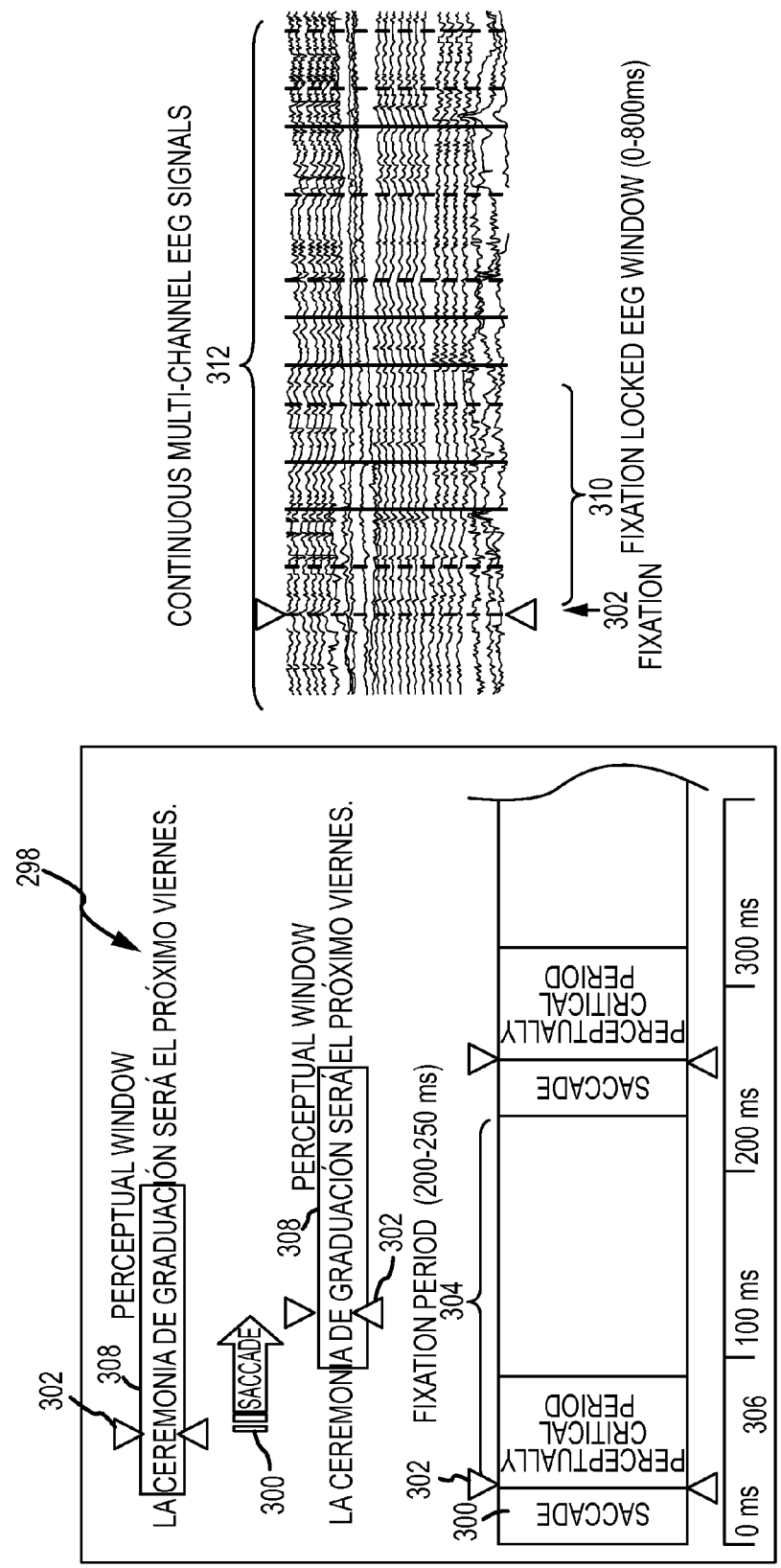

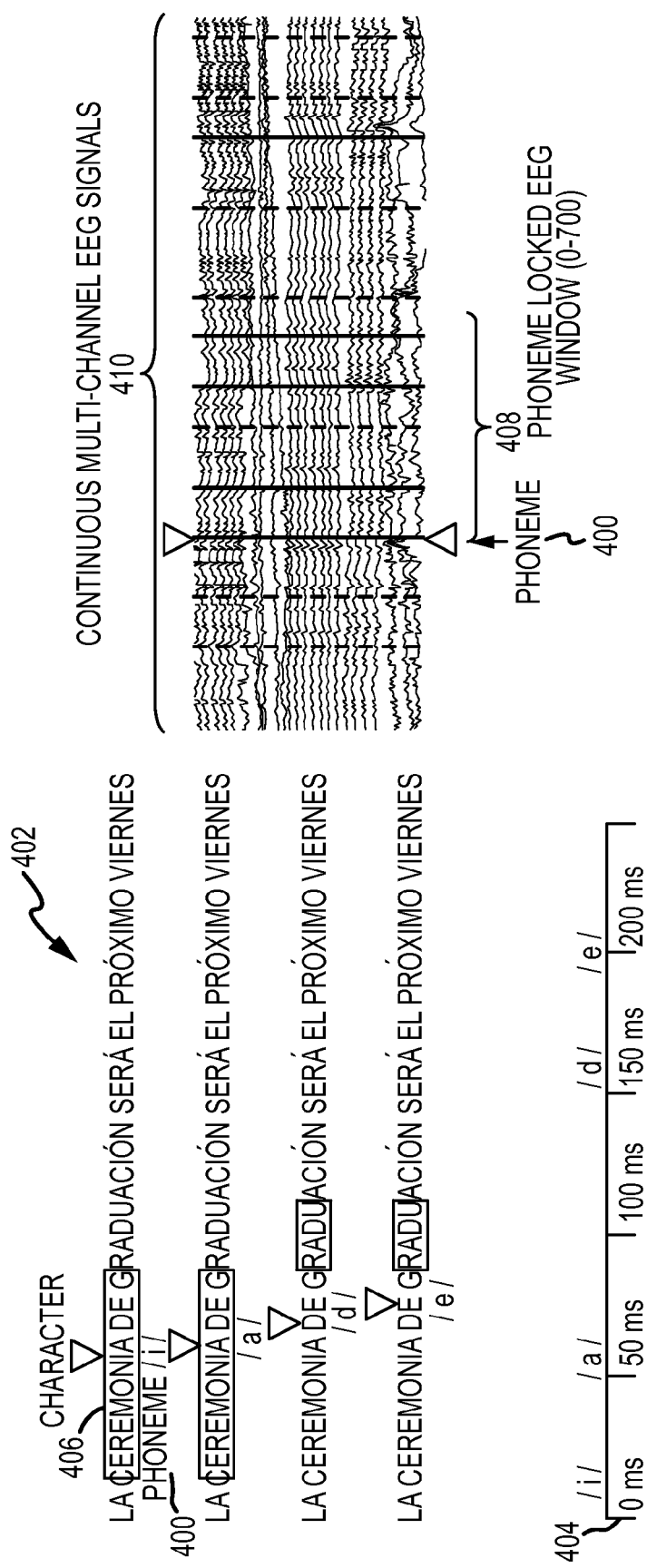

EEG-BASED ACCELERATION OF SECOND LANGUAGE LEARNING

BACKGROUND OF THE INVENTION

1. Field of the Invention

This invention relates to a computer-implemented system for second language learning and more specifically to augmenting such systems with single-trial measurements of a learner's brain response via electroencephalography (EEG) to the presentation of learning materials.

2. Description of the Related Art

Language-learning systems provide effective and non-traditional approaches for learners to learn a second language. Commercially available systems include Tell Me More®, Transparent Language® and Rosetta Stone® are in widespread use by organizations and individuals alike. These systems assess a learner's mastery of different language skills via oral or typed responses to isolate difficulties and adjust the lesson plans accordingly.

Rosetta Stone teaches definitions of words, grammatical distinctions, and formal structures by use of discrete lessons that each introduce or reinforce new language concepts. With each piece of new content, the learner progresses through a sequence of skills to work towards mastery. These skills include the written and audible comprehension of the new word or feature, pronouncing it correctly, and producing it both textually and vocally. The learner is assessed on each of these skills, so that the learner's difficulties can be isolated and more focused practice can be recommended. For example, a learner may pass the exercise that assesses their comprehension of a new vocabulary set, but may fail the exercise that assesses their ability to produce the new content. In this case, Rosetta Stone would recommend that the user repeat the failed exercise. Exercises vary between emphasizing the semantic content of an utterance (meaning) and isolating its syntactic features (rules for composition of words into phrases or sentences). Based on the learner's performance, it is therefore possible to determine whether their difficulty comes from comprehension of new vocabulary or a failure to grasp a new formal or grammatical feature. Rosetta Stone consists of hundreds of screens of content, each consisting of multiple images and various combinations of photo, text and audio stimuli that elicit a response from the learner indicating the their comprehension or correct utilization of a given linguistic feature (e.g., a vocabulary word, a grammatical structure).

Much of the academic research into the neuroscience of how language learning appears as brain activity via electroencephalography (EEG) has focused on Event-Related Potentials (ERP) associated with the processing of semantic and syntactic anomalies. An ERP is a measured brain response that is the result of a thought or perception that can be linked to an event. More formally, it is any stereotyped electrophysiological response to a stimulus. While evoked potentials reflect the processing of the physical stimulus, event-related potentials are caused by the brain processes that might involve perception, memory, expectation, attention, or changes in the mental state, among others. Though some ERP components in language learning are referred to with acronyms (e.g., early left anterior negativity—ELAN), most components are referred to by a preceding letter indicating polarity followed by the typical latency in milliseconds. Thus, the N400 ERP component is described as a negative voltage deflection occurring approximately 400 ms after stimulus onset, whereas the P600 component describes a positive voltage deflection 600 ms after stimulus onset. The stated latencies for ERP components are often quite variable; for example, the N400 component may exhibit latency between 300 ms-500 ms.

In native speakers, semantic anomalies elicit a negative waveform (N400) that peaks at 400 ms after an anomalous word [cf. Kutas & Van Petten 94]. N400 has also been observed for case-marking errors having thematic content in German [Friederici 04]. Left Anterior Negativity (LAN) waveforms have been observed 150-200 ms after the appearance of violation of local phrase structure, such as subject-verb mismatch. [Friederici 95] Late Centroparietal Positivity (P600) appears to arise in situations involving syntactic ambiguity, syntactic complexity and phrase structure violations [Osterhout & Holcomb, 1992; Friederici 04]. fMRI activation foci have been identified for syntactic violations, sentence processing, and syntactic memory in a number of studies [Friederici 04].

Several studies on second language learning demonstrate the appearance of N400 and P600 as markers of emerging language skill. N400 begins to appear in detection of non-words by adult French learners after only 14 hours of instruction [McLaughlin 04]. N400 responses to unusual word/word combinations (word followed by an unrelated word) begin to appear after approximately 62 hours of instruction. Discrimination between well-formed and ill-formed sentences in French elicits an N400 response (P600 is expected for native speakers) after 1 month of instruction. By 4 months of instruction, the N400 effect begins to disappear and is replaced by P600 [Ousterhout 04]. The magnitude of N400 has been hypothesized to reflect the difficulty of integrating multiple linguistic cues [Holcombe, 93]. N400 responses are present in beginning readers (L1) even for ordinary, error-free text [Cock & Holcombe, 2006]. These ERP markers are detected using grand averaging schemes over many trials to detect the emerging language skills.

SUMMARY OF THE INVENTION

The present invention provides for EEG-based acceleration of second language learning.

This is accomplished by measuring via single-trial EEG a learner's cognitive response to the presentation (visual or auditory) of language learning materials and updating a user model of latent traits related to language-learning skills in accordance with the cognitive response. The updated states of the latent traits provide indicators of the learner's language-learning skills that may be used to modify subsequent lessons. The user model is suitably updated with each trial, each trial being triggered by learner fixation on a portion of visual materials and/or a next phoneme in auditory materials. Measurement and analysis of the latent trait(s) tested by each perceptual window that follows a fixation or phoneme provides both a large number of trials and a high level of discrimination. EEG-based learning may be used independently or in conjunction with learning provided by a more conventional analysis of a learner's motor response (auditory or typed) to the materials.

In an embodiment, a lesson of language-learning materials is presented on a display to elicit a response from a learner. The materials are presented on the display so that the learner is allowed to move his or her eyes freely in response to the displayed materials. EEG data of the learner's brain activity is measured from a plurality of electrodes placed on the learner's scalp. The learner's eye movements are tracked to provide position signals that are processed to determine fixation events on the materials. A fixation-locked window is applied to the EEG data to generate a time segment of EEG data for each fixation event. For each fixation event, one or more features are extracted from the time segment of EEG data. For each fixation event, the features are presented to a classifier to generate a fixation-locked cue indicative of whether the learner exhibited a significant cognitive response to the displayed materials. The cues are synchronized to the associated portion of the displayed materials. For each fixation event, one or more latent traits tested by the presentation of the materials are retrieved and paired with the cue to update a user model of latent traits. The updated states of the latent traits provide indicators of the learner's language-learning performance.

In another embodiment, the learner's motor responses, either typed or auditory, to the presentation of the language-learning materials are recorded and analyzed to provide indicators of the learner's language-learning performance. The EEG-based and motor response-based indicators are combined to assess the learner's language-learning performance and used to modify subsequent lessons.

In another embodiment, the position signals are also processed to provide measures of saccades or fixation duration. These measures provide additional information to update the latent traits in the user model.

In another embodiment, each latent trait is described by a probability distribution that relates the trait to a cognitive response, possibly one or more specific ERPs. A Bayesian network infers which latent trait caused the cognitive response to update the user model.

In another embodiment, the states of the user model are used to modify the presentation or content of subsequent lessons.

In another embodiment, the classifier is configured to identify a specific ERP or temporal pattern of ERPs associated with the learner's cognitive brain response.

In another embodiment, the classifier is a spatio-temporal classifier that comprises a plurality of multi-channel spatial sub-classifiers and a temporal classifier. Each multi-channel sub-classifier is trained to detect spatial patterns of extracted features during a specific narrow window offset from fixation. Each window has a different offset and together they span the entire window. The temporal classifier combines the outputs of the spatial sub-classifiers to detect temporal patterns across the different time windows relating to the evolution of the non-stationary brain response to stimuli and generate a cue indicative of the occurrence or absence of significant brain response. The temporal windows may be tuned to correspond to different ERPs such as ELAN, LAN, N400 and P600.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 1a and 1b are diagrams of an EEG accelerated language-learning system;

FIGS. 5a and 5b are diagrams of a fixation-locked window of language materials and the fixation-locked processing of the EEG signals;

FIGS. 6a and 6b are diagrams of a phoneme-locked window of language materials and time tags and the phoneme-locked processing of the EEG signals;

DETAILED DESCRIPTION OF THE INVENTION

Figure 1B:
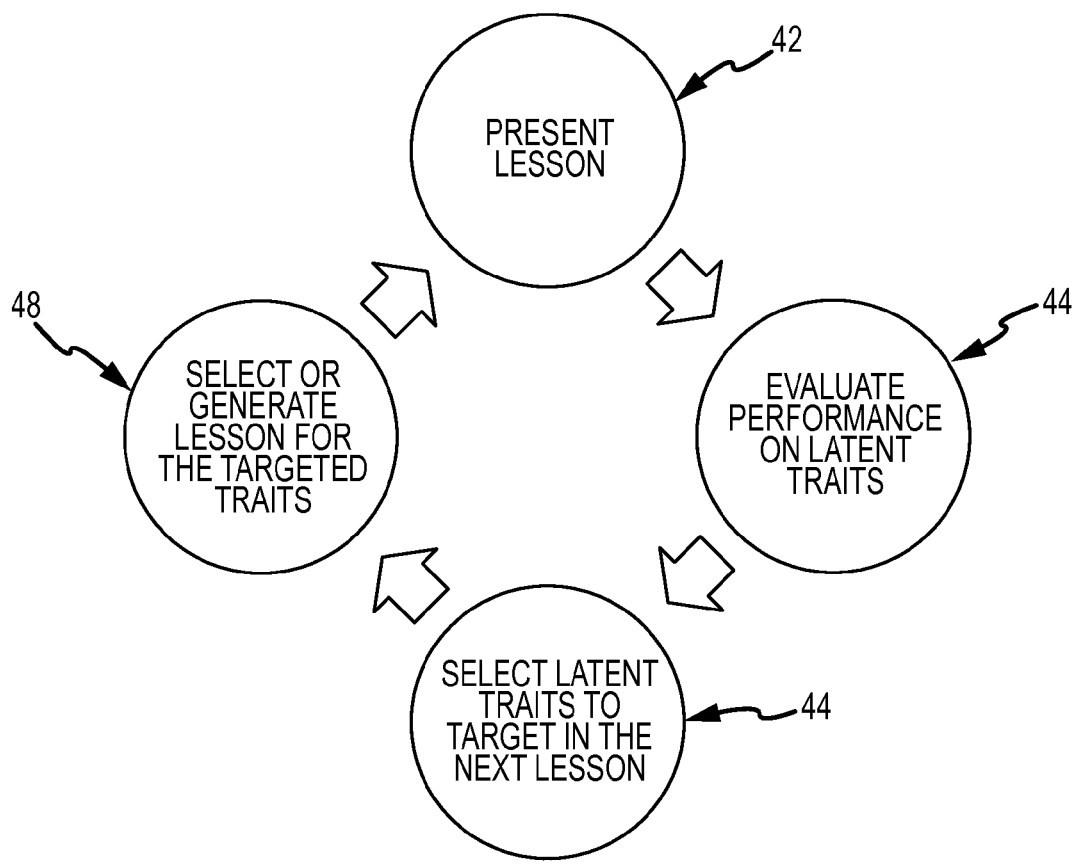

EEG analysis dramatically increases the information collected from a learner during language learning and the evidence available to discern the source of learning difficulty. Interactive language-learning systems collect only the learner's typed or spoken responses to specific language queries. An EEG-based approach assesses language-learning performance continuously with every fixation (eye movement) and phoneme (atomic component of audible speech) and correlates each brain response with the skills tested by a specific portion of the lesson.

EEG-based acceleration of second-language learning is accomplished by measuring via single-trial EEG a learner's cognitive response to the presentation (visual or auditory) of language-learning materials and updating a user model of latent traits related to language-learning skills in accordance with the cognitive response. The cognitive response may be associated with a specific ERP or temporal pattern of ERPs. The updated states of the latent traits provide indicators of the learner's language-learning skills that may be used to modify subsequent lessons. The user model is suitably updated with each trial, each trial being triggered by learner fixation on a portion of visual materials and/or a next phoneme in auditory materials. Measurement and analysis of the latent trait(s) tested by each perceptual window that follows a fixation or phoneme provides both a large number of trials and a high-level of discrimination for language-learning difficulties. Additional discrimination may be achieved through the use of saccades or fixation duration features. EEG-based learning may be used independently or in conjunction with learning provided by a more conventional analysis of a learner's motor response (auditory or typed) in response to the materials.

Without loss of generality, EEG-based acceleration of second-language learning will be described in conjunction with Rosetta Stone®. Since Rosetta Stone presents the learner with thousands of stimuli in the target language and instant feedback regarding the learner's comprehension or production of a given feature of the target language, Rosetta Stone provides a suitable environment for the evaluation of neurological responses to difficulties in language acquisition. Rosetta Stone assesses both the learner's comprehension and production of the semantic features of the language as well as the learner's comprehension and production of its syntactic features. Thus Rosetta Stone provides both suitable control (tracking learner motor response to learning inputs) as well as an environment for EEG-based acceleration. It will be understood by those skilled in the art that EEG-based acceleration may be configured for use with other language-learning systems.

Referring now to FIG. 1a, an embodiment of an EEG accelerated language-learning system 10 comprises the hardware and software modules of the language-learning system (e.g. Rosetta Stone®) plus additional hardware and software modules to implement the EEG-based acceleration.

The language-learning system itself comprises one or more computers 14 including one or more processors 16 and memory 18. A language-learning module 20 including a language knowledge base of visual and audio lessons 21 resides in memory. Language-learning module 20 is executed by the processors to render the visual language lessons on a display 22 and the audio language lessons through headphones 24 (or audio speakers). The module acquires data from the learner for elicited responses via a keyboard and mouse 26 or a microphone 28. The module evaluates the learner's motor responses to assess the learner's strengths and weaknesses of various language-learning skills and determine subsequent lessons.

The EEG-based enhancement system comprises a cap of EEG electrodes 30 placed on the learner's scalp to continuously provide multi-channel EEG signals and an eye tracker 32 such as a camera(s) that provide position signals to determine fixation-events and the corresponding fixation points (gaze position on the reading material) of the learner. The eye position signals may also be processed to provide measurements of saccades (ballistic eye movements between fixations) or fixation durations.

An EEG acceleration module 33 comprises a user model 34 of stored latent traits of the learner's language-learning skills. A latent trait is a property of something that cannot be observed directly, in our case language learning skills of the learner. Latent traits may include understanding specific vocabulary, understanding specific pronoun-verb agreement rules, etc. The term latent trait comes from "Item Response Theory." The user model may be based on Item Response Theory or other acceptable models. Item Response Theory is not a required component of EEG accelerated second language learning.

A classification module 36 processes stimulus-locked (e.g. fixation or phoneme) single-trial EEG signals to generate a sequence of cues that indicate cognitive brain response of the learner to the lesson (possibly classifying the response as a particular ERP or temporal sequence of ERPs). EEG signals represent the aggregate activity of hundreds of thousands (~150K) cortical pyramid cells and have high time-resolution (capable of detecting changes in electrical activity in the brain on a millisecond-level). The brain response to stimuli reflects neurophysiological activities located in selectively distributed sites of the brain evolving with a continuous time course. The brain response to an "event" is a non-stationary signal distributed across multiple areas of the brain. Specifically, perceptual information from the senses is first processed in primary sensory cortex from where it travels to multiple cortical mid-section areas associated with separately processing the spatial ("Where") and semantic ("What") meaning of the information. The resulting information patterns are matched against expectations, relevance or mismatch at which point signals are relayed to more frontal regions were higher-level decisions can be made about the relevance of the information. If enough evidence exists, a commitment to respond is then made. This suggests that the decision process involves multiple sites (space) across a relative long time window. Stimulus-locked measurement and classification of the evolving temporal signature of the EEG signals allows for single-trial detection of cognitive responses. The classifier may be trained to not only detect the overall cognitive response but to identify the ERP or temporal pattern of ERPs associated with the response.

An inference engine 38 uses the cues from the EEG classification, saccades, fixation durations and learner responses as observations of the one or more latent traits tested by the corresponding lesson materials to infer a state of the trait(s).

In an embodiment, the inference engine is implemented as a Bayesian network. Each latent trait is represented by a simple Bayesian network model that may include the EEG cue, specific ERP scores (magnitudes of ERP components), saccades, fixation durations and motor responses. This simple model provides a probability distribution for each type of response for each latent trait. If a single latent trait is tested, the inference engine infers the state of that trait from the cue(s). In a more typical case, it is impossible to completely disambiguate all of the latent traits present in a sentence; for example, a specific phrase may test the understanding of multiple words and grammatical features.

When multiple latent traits are tested, the inference engine uses a "noisy max" technique to infer the state of the latent trait that caused the response. A presentation history for each latent trait is suitably stored. The inference engine retrieves the presentation history for a trait and uses it to compute a prior probability distribution for the latent trait using a forgetting curve. The forgetting curve captures the probability that you recall a fact given how well you know it (latent trait strength) and the history of presentation (how many presentations). EEG spectral signatures may be analyzed to determine if the learner is paying attention. This information can be used to discard data, alert the learner or to modify the presentation of lessons to better maintain the learner's attention.

A lesson customization module 40 customizes lessons based on the current states of the user model.

Referring now to FIG. 1b, language-learning module 20 presents a lesson to the learner (step 42) through some combination of audio and visual materials typically posing questions to illicit a motor response (typed or auditory) of the learner. The language-learning module 20 and EEG acceleration module 33 monitor the motor and EEG responses (and saccades, fixation duration, EEG spectral response), respectively, to evaluate performance on latent traits (step 44). The modules select the latent traits to target in the next lesson (step 46) and based at least in part on the current state of the user module generates a lesson for the targeted traits (step 48). In an alternative embodiment, only the EEG cues and the updates to the user model are used to customize the lesson plan without regard to the learner's motor responses to the lesson. The EEG cues may be augmented by EEG spectral analysis or measures of the saccades or fixation duration.

By continuously monitoring each and every stimulus-locked (fixation or phoneme) cognitive response of the learner to the lesson we dramatically increase the information collected from the learner during language learning thus increasing the evidence to identify the source of any learning difficulties.

Furthermore the information is specifically targeted to individual latent traits thereby enhancing the discrimination capability to isolate strengths and weaknesses of the learner.

This information can be used to repeat previous lessons at targeted latent traits, to modify how lessons are presented to improve learning effectiveness, to modify the contents of lessons, to modify how feedback or "rewards" is presented to the user and to improve attention. The use of stimulus-locked EEG accelerates second language learning.

Figure 2:
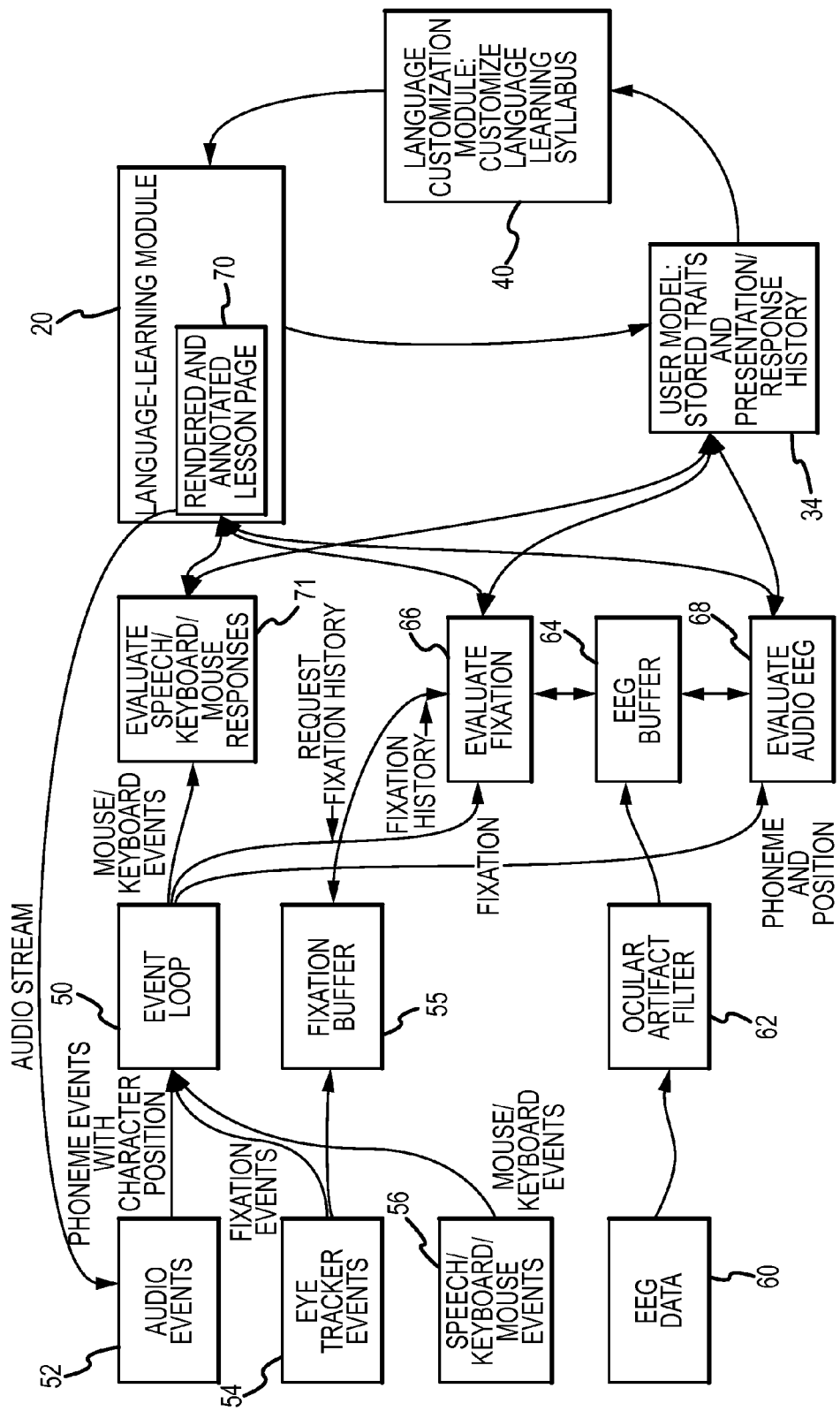
FIG. 2 is a flow diagram of an event-loop for the EEG-based accelerated language-learning system.

Referring now to FIG. 2, the EEG accelerated language-learning system is driven by an event-loop 50 that intercepts synchronizing audio and fixation events, along with keyboard and mouse events. Audio events 52 identify the rendered phoneme and include the time and a pointer to the location of the phoneme in the associated language lesson. Audio events can be generated by a speech synthesizer (for automatically generated speech), on-line speech recognition (for recorded speech) or via off-line automated or manual annotation of recorded language segments. Eye-movement events 54 are fixations, including the time of fixation and screen coordinates for the gaze center. During evaluation, the visual representation of the language lesson is searched to determine the word fixated. Eye-movement events are placed into a fixation buffer 55 that is used to determine saccade direction and duration. Eye-movement is not limited to eye trackers implemented with cameras—it can be any system that tracks the fixation point for the eye. Both audio and eye tracker events produce "stimulus-locked" events. Speech, keyboard and mouse events 56 include time-stamped gestures used ordinarily to register learner responses to questions or selections. These are the standard ways to respond to language software developed by many companies (for example, Rosetta Stone) and are well understood by those in the art. All of the events go into event loop 50 that processes them in order of receipt.

Multi-channel EEG data 60 is recorded continuously through the language learning process. After ocular artifacts are removed by a filter 62, the data is windowed according to the stimulus-locked events and placed into an EEG buffer 64 for classification and frequency-component analysis. For example, a time segment of 800 ms of data measured from fixation or the phoneme is placed in the buffer. The EEG acceleration module, particularly the classification module and inference engine, evaluates fixation 66 to update the user model using fixation-locked cues of learner cognitive response inferred from the EEG buffer. These cues may be associated with specific event-related potentials. The module may also update the user model using saccade direction/distance (inferred from the history of fixations as well as the presented material) and fixation duration. The EEG module evaluates audio EEG 68 to, for example, analyze the spatiotemporal EEG pattern for the first 700-800 milliseconds following each phoneme (phoneme-locked ERP) and update the latent traits in the user model associated with the phoneme. The potential could also be locked to the syllable. Frequency components (notably the alpha band from 8-12 Hz in the posterior region of the head) are used to determine how well the subject is attending to the signal.

Language-learning module 20 renders the lesson 70 to present language learning materials to the learner and evaluates Speech/Keyboard/Mouse responses 71 in the context of the current language lesson and updates the user model in response to standard language software events. Visual elements are rendered to the display and audio elements, provided as recordings or speech synthesizer input, are rendered to the headphones or a speaker. Latent traits tested by the language software can be part of the language lesson, or can be externally defined and then inferred from the language lesson file. These latent traits represent distinct skills associated with language learning, including word meaning(s) and grammatical structures. The language-learning module can change the order of presentation for topics or construct lessons from observed language deficiencies recorded in the user model.

User model 34 contains the presentation history for each latent trait and the probability distribution over the latent trait's value. The presentation history is used to determine parameters in the forgetting model. The latent traits' values or "state" are continuously updated by the standard ways to evaluate learner motor responses to the presented materials and the stimulation-locked EEG cues. In an embodiment, the user model and inference engine are based on a Bayesian network framework. The user model consists of probability distributions that relate each trait to different observations including the standard motor responses and EEG cues. The model may relate the latent traits to specific ERPs. The probability distributions may be manually-assigned by an expert, automatically assigned using Bayesian clustering or latent variable learning techniques to learn the model for the occurrence of EEG components given classes of morphosyntactic features or some combination thereof. The inference engine processes the observations (e.g. cues and motor responses) to determine which latent traits caused the response or was likely to cause the response. The inference engine may use a "noisy max" technique to identify the latent traits when the tested materials (as is often the case) relate to multiple latent traits.

Lesson customization module 40 customizes the language learning syllabus for subsequent lessons based on the user model.

Figure 3A:
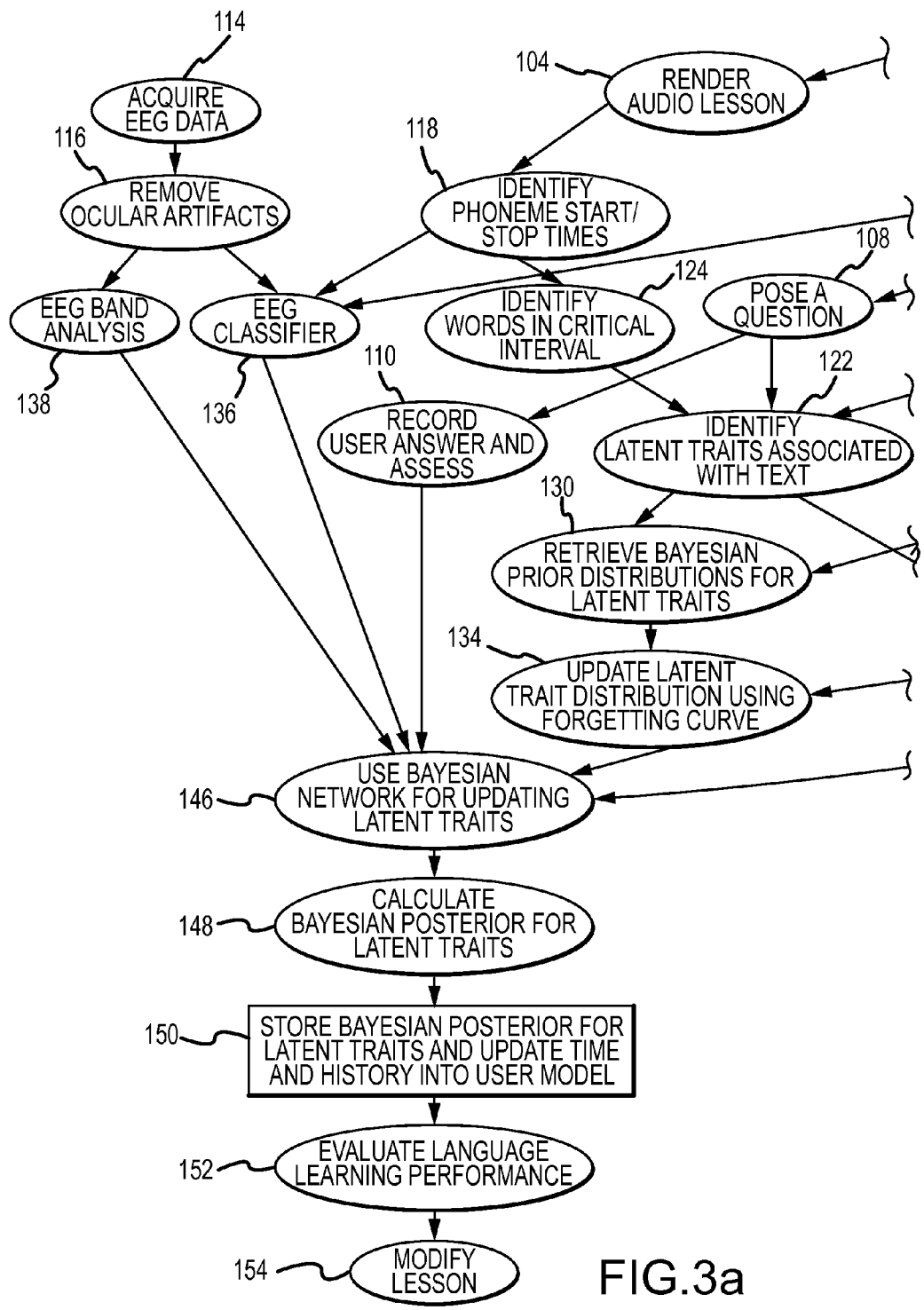
FIGS. 3a and 3b are a flow diagram of an embodiment of the language-learning system.
Figure 3B:
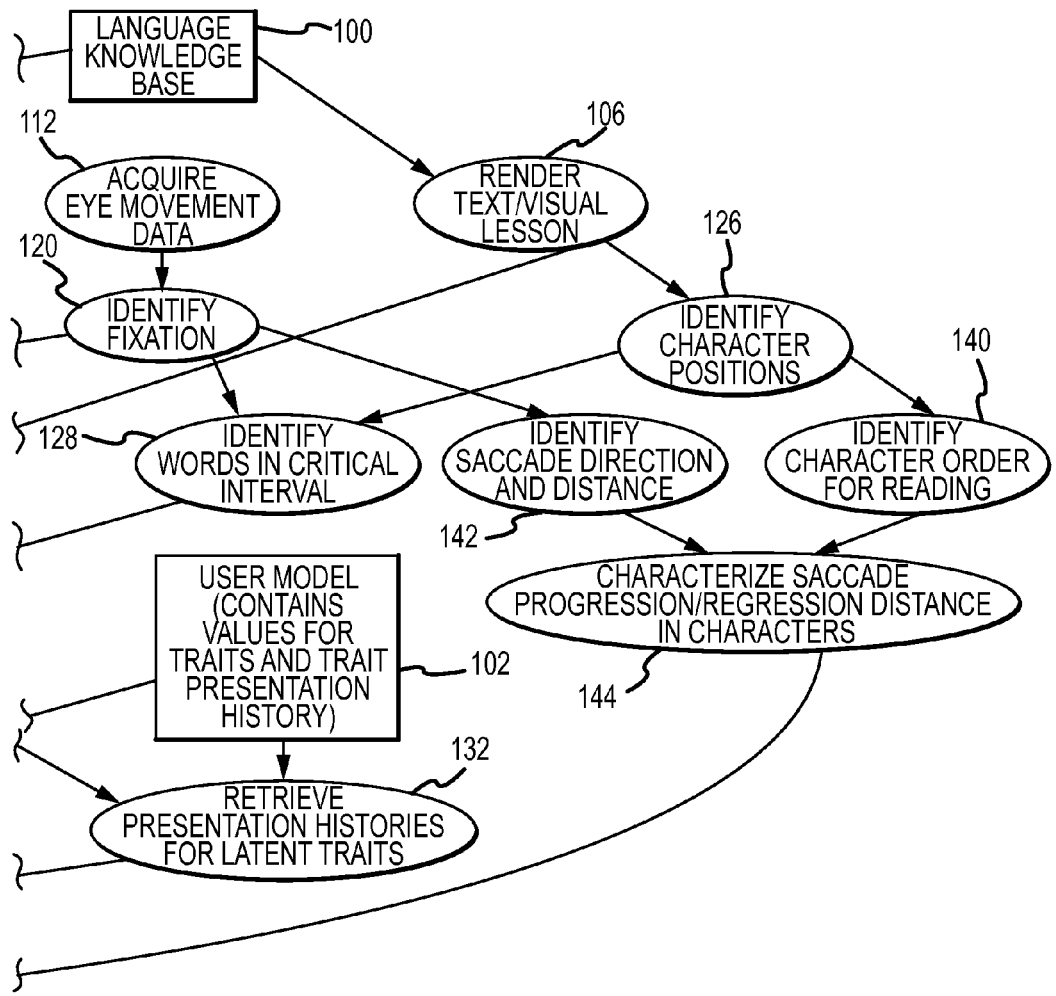

An embodiment of EEG accelerated second language learning using a Bayesian network that incorporates standard motor responses, both fixation-locked and phoneme-locked EEG classification, saccades/fixation duration and EEG band analysis to evaluate latent traits of language learning skills to update a user model and customize lessons is illustrated in FIGS. 3a and 3b.

The central components include a language knowledge base 100 that is provided by the lesson-learning module and a user model 102 that is provided by the EEG module. The language knowledge base 100 provides the language-learning materials that are presented as lessons to the learner (the "input") and the user model 102 represents the state of the learner's mastery of the language for a number of specific skills, more specifically the values or "states" for the latent traits and trait presentation history (the "output"). The remaining steps are directed at how materials are presented and data is acquired and processed to update the user model to customize further lessons for the learner.

The language-learning module renders both audio materials (step 104) via headphones or audio speakers and visual materials, text or images (step 106) on a display. Often times the visual materials will pose a question (step 108) to illicit a motor response, typed or spoken, from the learner. The learner answer is recorded and assessed (step 110) to update the user model using known techniques for language-learning programs such as Rosetta Stone.

Eye-movement data (step 112) and multi-channel EEG signal data (step 114) is continuously acquired during the presentation of language-learning materials. The EEG data is suitably processed to remove ocular artifacts (e.g. blinks or eye movement) (step 116).

To both process the data to extract meaningful observations and to accurately correlate those observations to the associated latent traits, the extraction and processing of the data is locked to the stimulus. We lock to the stimulus by identifying the phoneme start/stop times (step 118) and identifying fixations (step 120) from the eye movement data. We process each time segment of data that follows a stimulus, either a fixation on visual materials or phoneme in the audio materials, and correlate the brain response to that stimulus to the one or more latent traits tested by the stimulus. By using a stimulus-locked approach we can better classify the EEG data in a single-trial (without grand averaging) and better discriminate individual latent traits.

To identify latent traits tested by spoken or visual text (step 122), the module identifies words in a critical interval around each phoneme (step 124). The critical interval around each phoneme includes the word containing the phoneme as well as morphosyntactic grammatical features that terminate in the word. The module identifies character positions of displayed text (step 126) and correlates those positions to positions on the display associated with fixation to identify word in a critical interval (perceptual window) around each fixation (step 128). The critical interval around a fixation point extends from approximately 3 characters to the left of fixation to 14 characters to the right of fixation in a left-to-right language such as English or German [cf. Rayner 1998].

Latent traits may be associated with any question posed by the materials (step 108).

The probability distributions over the values for each latent trait "tested" by the presentation materials is retrieved (step 130) from user model 102 along with the presentation history for each trait (step 132). Periodically, the prior probability of the distribution is updated using a forgetting curve (step 134) that adjusts the prior distribution to reflect the decay of memory with time. Ebbinghaus suggested a simple forgetting curve of the form $$\theta_{trait,t_s} = \theta_{trait,t_e} e^{\frac{(t_t - t_s)}{S}},$$

where S is the strength of the memory. We assume a simple model where the strength of a memory is the number of prior lessons demonstrating the concept. In this embodiment S=KN, where K is a constant on the order of 2E6, if time is measured in seconds and N is the number of previous lessons containing the concept. This forgetting constant suggests that the memory for a trait will decay by 20% after 1 week, provided that it is presented only once. Different forms of the forgetting model exist and may be used.

Prior to inference, the distribution is suitably modified over the traits to ensure that the probability density is everywhere above a small constant. This ensures that there are no zeros in the distribution for any tested trait. If the prior distribution is zero for some value of the trait, then the posterior distribution of the trait will be zero for that value, regardless of the amount of or distribution of measurements. By adding a small constant to the full distribution, we allow the EEG and question answering evidence to show that a concept has been learned or forgotten no matter what the past history might indicate.

Single-trial analysis of the stimulus-locked EEG data and eye movement data generates observations of the latent traits to augment the observations provided by assessment of the learner's motor responses to questions posed. The multi-channel EEG data and time-codes for the fixations and phonemes are presented to an EEG classifier (step 136). The classifier extracts features (e.g. spatial, temporal, frequency or other such as through an independent components analysis ICA) from a window of the EEG data following the fixation or phoneme and classifies the pattern of features to generate a stimulus-locked cue indicative of whether the learner exhibited a significant cognitive response to the displayed materials. The classifier may be configured to identify a specific ERP (e.g. ELAN, N400, P600, etc.) or temporal pattern of ERPs with a positive cue. Identification of specific ERPs may provide more information regarding the underlying latent trait(s) that caused the positive cognitive response. In other words, the specific ERPs provide additional evidence discriminating between the sources of misunderstanding. An EEG spectral band analysis of the EEG is performed (step 138) to determine the power contained in the 8-12 Hz band (the alpha band). When power in the alpha band is above a threshold, the module assumes that the learner is not paying attention and the observation is discarded. This measure may also be used to modify the lesson content or how lessons are presented to maintainer a learner's attention.

Saccades also reveal information about language comprehension. To measure saccades and fixation durations, the module identifies character order for reading (step 140) and saccade direction and distance (step 142) and uses them to characterize saccade progression/regression distance in characters and to calculate fixation durations (step 144). Based on statistics for native-language learning, a likelihood of error can be assigned based on the length of a saccade and whether it is a regression or a progression and a likelihood of error can be assigned based on the length of fixation. Saccades provide additional cues for the diagnosis of language-learning ability. Eye movements are an established paradigm for reading research, yet it does not appear that eye movement has been studied extensively in the context of second-language learning. A fluent native language reader reads approximately 280 words per minute. A fluent reader fixates on text for 200-250 ms (with a normal variation of 150 to 500 ms), then saccades to a new foveation point, progressing 6-9 characters with each saccade. In fluent readers saccades regress approximately 10-15% of the time. While saccades vary from 1 to 20 characters, longer saccades typically follow regressions [Reichle, et al 2004]. Beginning native language readers exhibit smaller saccades, longer fixations and more regressions. Both beginning and fluent readers fixate longer on difficult words. Increases in fixation or regression in a text passage provide additional cues that allow us to distinguish between sources of grammatical difficulty [Frenck-Mestre, 2005].

One strategy for using eye movements is to use Markov Chain Monte-Carlo reasoning to infer the familiarity of a word (as measured by word frequency) using a generative model, such as the E-Z Reader model [Reichle, et al 2006]. The E-Z Reader model is a stochastic model that predicts eye movements during reading as a function of word length $L_i$ and word frequency $F_i$, that is, it computes the probability of a fixation sequence S given word length and word familiarity, that is $P\{S|L_i,F_i\}$. Markov-Chain Monte Carlo can compute the distribution over word frequency (proxy for familiarity) given the saccade sequence and the word length and sequence $P\{F_i|S,L_i\}$. Another strategy is to use specific saccades to diagnose problems. Long regressions are frequently a sign that a concept or word is misunderstood. The target of a saccade is likely to be a misunderstood word or a word contributing to an unfamiliar grammatical structure.

A Bayesian network (one instantiation of the inference engine) is used to update the latent trait distribution (step 146) given the observation of EEG cues (possibly scores for specific ERPs), saccades, fixation durations, EEG alpha measures and assessed learner responses to the posed questions. Several traits may be tested in a single fixation. In order to generalize the assessed single trait probability distributions, we use a canonical distribution called a noisy max distribution [Henrion, 89]. The idea is the following: consider that several traits are or may be the cause for a specific EEG component—the resulting coefficient for the measured EEG component is assumed to be the max of the coefficients for the individual EEG components. The resulting response is assumed to be the maximum of the responses generated by individual latent traits. Fixation duration is assumed to be the maximum of the fixation durations that would be caused by each relevant latent trait and saccade length is assumed to be the minimum of the saccade lengths that would be caused by each latent trait. The network calculates the Bayesian posterior distribution for the latent traits (step 148) using, for example, a Markov-Chain Monte Carlo approach and stores the posterior distribution and updated presentation history into the user model (step 150).

As mentioned previously the classifier may be configured to associate an ERP or temporal sequence of ERP with the cue to provide additional evidence to discriminate the sources of any learner misunderstanding. This additional evidence assists the Bayesian network to correctly identify the latent trait that causes the cognitive response. Because these ERPs are measured relative to the presentation of the stimulus, our technique for stimulus-locked processing and classification of the EEG data is well suited to classify specific ERPs.

Research on language learning and second language learning (L2) focuses on four event-related potentials that have been identified with language processing for L1 (the speaker's native language):

ELAN: Early left anterior negativity, which presents 100-300 ms after a syntactic anomaly such as a phrase structure violation [Friederici 2002].

LAN: Left anterior negativity presents 300-500 ms and is a measure of morphosyntactic error [Friederici 2002]

N400: Centro-parietal negativity peaking 400 ms after a semantic anomaly [Kutas & Hilyard 1980]

P600: Centro-parietal positivity peaking 600 ms after a syntactic anomaly, possibly reflecting syntax checking/repair activities.

There is considerable variability in the presentation of these ERPs in second language (L2) processing. Weber and Lavric [08] demonstrated that an N400 manifests in L2 English speakers in response to syntactic anomalies, but that is absent in L1 English speakers. Other studies show that the P600 develops in L2 speakers with high proficiency [Hahne 01; cited in Mueller 09]. Osterhout, et al [09; cited in Mueller 09] theorize that N400 is generated instead of a P600 because L2 speakers are thought to have memorized templated forms in early learning instead of more general morphosyntactic rules [Osterhout 09; cited in Mueller 09].

The primary diagnostics of performance are therefore:

In error-free text, the N400 appears for unfamiliar concepts and disappears once they are well known.

in error-free text, the P600 appears for unfamiliar syntactic structures once language rules are automatized (very experienced L2 speaker).

When there are syntax errors in learning corpus, undetected errors elicit no response and detected errors elicit an N400 early and a P600 once grammar rules are automatized (very experienced L2 speaker).

When there are semantic errors in learning corpus, undetected errors elicit no response and detected errors elicit an N400.

Phrase or other local morphosyntactic errors in learning corpus: Detected errors elicit a LAN or ELAN, but only in very experienced speakers. [Rossi 96, Hahne 06; cited in Mueller 09]

The lesson customization module monitors the states of the latent traits (e.g. specific values of probability distributions) in the user module to evaluate language-learning performance (step 152). The module can assess the mastery or difficulty a learner is having with specific skills. The module can also assess whether these skills are improving, staying flat or even degrading. The module uses this information to modify the lessons (step 154) in the language knowledge base 100 and when and how they are presented to the learner. The entire analysis may be performed either in real-time during language learning or after a language lesson has been completed.

Referring now to FIGS. 4 through 8, stimulus-locked measurement and classification of the evolving temporal signature of the EEG signals allows for single-trial detection of cognitive responses, possibly specific ERPs, and correlation to the tested latent traits, hence the continuous updating of the user model.

Figure 4:
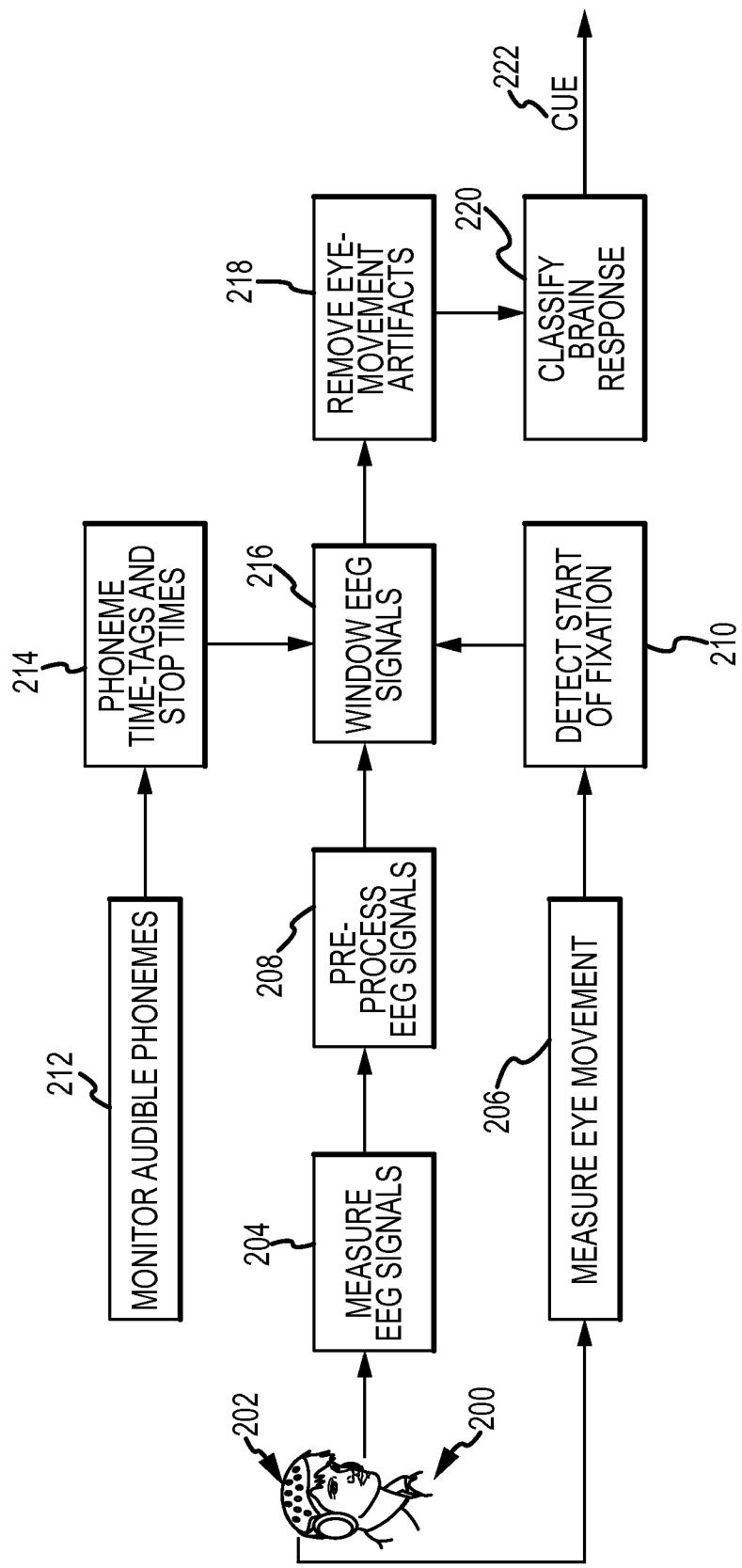
FIG. 4 is a diagram of any embodiment for fixation or phoneme-locked processing of EEG signals to generate an output cue indicative of whether the learner exhibits a significant cognitive response the presentation materials.

As shown in FIG. 4, a learner 200 outfitted with a cognitive monitoring device (CMD) 202 for monitoring, classifying and transmitting cues based on the learner's cognitive responses to stimuli in the form of audio and visual language learning materials. The CMD is also configured to monitor eye movement and determine fixation on displayed text. The functions of the CMD may be integrated within device worn by the learner or separated between the device and one or more separate computers that implement the language-learning and EEG acceleration modules.

As the learner 200 reads the displayed text, CMD 202 measures the learner's EEG signals (step 204) and eye movements (step 206). The EEG signals may be pre-processed (step 208) to remove large artifacts such as those from eye blinks and head movements and band pass filtered to reduce noise. The learner's eye movement is monitored to detect the start of fixation e.g. a "fixation event" (step 210). Audible phonemes are monitored (step 212) to detect phoneme start/stop time tags e.g. a "phoneme event" (step 214). Each fixation or phoneme event provides a marker to time window the EEG signals (step 216). The windowed EEG signals are suitably processed to reduce artifacts and mitigate noise due to eye movement (step 218). Each time segment of stimulus-locked windowed EEG signals is classified to determine if there is a significant cognitive response to a relevant stimulus (step 220). Stimulation-locked measurement is a single-trial process in which each fixation-event or phoneme-event produces an output cue 222. The sequence of cues 222 is suitably time-stamped with the time-code of associated fixation-event or phoneme-event to facilitate correlation with the latest traits that are extracted. The cue may be a binary decision (0 or 1) or assigned a likelihood (0-1 or 0 to 100%) that a significant cognitive response occurred. The cue may be a generic indicator of cognitive response or may include a tag classifying the stimulus or the nature of the brain response. For example, the tag might indicate the particular ERP (e.g. ELAN, P300, P600).

An embodiment of CMD 202 includes electrodes placed on the learner's scalp to generate multiple spatial channels of EEG signals, each spatial channel including a high-resolution temporal signal typically representative of an amplitude difference between a pair of electrodes. An eye-tracker measures the instantaneous position of the eyes by detecting the pupil (as the detection of light reflected off the back of the retina due to the near infrared (NIR) light projected onto the eye). The measure of the diameter may provide pupil size signals. The measure of the position of the eyes provides the position signals. With the position sampled at high rates, one can determine the instantaneous displacement. If the displacement, measured as a change in position or derivatives such as the velocity, surpasses a reasonable small threshold, it means that the eyes are moving. A resumption of the stable position indicates a fixation.

Although it is understood that all processing could be integrated into a single processor or allocated among a plurality of processors in a variety of ways, for clarity signal processing is divided among several functional processors. A fixation processor monitors the position signals to determine fixation on a particular stimulus. Fixation occurs when the eyes remain focused on a constrained spatial region of, for example, less than half a degree. A phoneme processor monitors the audio signals to detect the start/stop time tags of each phoneme. A signal processor pre-processes the raw EEG signals using the position signals to remove artifacts due to blinks and head movement, segments the signals into a sequence of stimulus-locked time windows (possibly overlapping) and processes each segment of EEG data to reduce eye movement artifacts noise. Artifact removal for head movement and blinks is well known. A technique for removal of blink artifacts is described in Lucas C. Parra et al. "Response Error Correction—A Demonstration of Improved Human-Machine Performance Using Real-Time EEG monitoring" IEEE Trans. On Neural Systems and Rehabilitation Engineering, Vol. 11, No. 2, June 2003, which is hereby incorporated by reference. A technique for removal of eye movement artifacts is described in German Gomez-Herrero "Automatic Removal of Ocular Artifacts in the EEG without an EOG Reference Channel", Proc. of the $7^{th}$ Nordic Sig. Proc. Symp., pp. 130-133, 7-9 Jun. 2006, which is hereby incorporated by reference. A clock provides a clocking signal the signal processor uses to assign a time-stamp to each signal sample and fixation. A cognitive response processor extracts features from each segment of windowed EEG data and classifies the data to provide a cue and time-stamp. The cue and time-stamp are correlated with the retrieved latent traits and presented to the Bayesian network to update the probability distribution of the latent traits in the user model.

Stimulus-locked processing of the EEG data facilitates classification of the cognitive brain response for each fixation-event and each phoneme. By knowing precisely when the stimulus is presented, the classifier can be configured and trained to more robustly detect cognitive responses to that stimulus. Such single-trial processing allow for individual cognitive responses to stimuli to be paired with the one or more latent traits that produce the response. Such processing may also provide for labeling each response with the ERP or temporal sequence of ERPs that caused the response. This provides additional evidence to accurately discriminate the source of language-learning misunderstanding. Updating the user model for each fixation-event and phoneme-event aggregates a large number of observations so that the user model more-accurately represents the learner's strengths and weaknesses in language-learning skills.

Referring now to FIGS. 5a and 5b, during reading of a lesson 298 the eye typically saccades 300 (20-35 ms) forward ~6-9 characters before fixating 302 for a period 200-250 ms 304 (100-500 ms normal variation) [Raynor, 98]. The first 50-60 ms of fixation is the perceptually critical period 306. Temporal windowing experiments reveal that reading speed and comprehension is not impaired if fixated text disappears after this period [Ishida & Ikeda 89]. A person cannot fixate on any one spot for more than a few hundred milliseconds. Even if a person stares at one spot the eye will saccade back and forth and re-fixate albeit in approximately the same direction. For readers of English, the perceptual window 308 extends from 3-4 letters to the left of fixation 302 to 14-15 characters to the right of fixation [Rayner 98]. We synchronize EEG analysis to the start of the perceptually critical period 306 (start of the fixation 302) by applying a fixation-locked EEG window 310 to the continuous multi-channel EEG signals 312 starting at fixation. EEG analysis is assumed to pertain to the words that intersect with the perceptual window 308 as well as grammatical traits (subject noun agreement, for example) that terminate in the perceptual window. The output cues of the EEG analysis are correlated with the latent traits associated with the text in the perceptual window 308. This process is suitably repeated for each and every fixation.

Referring now to FIGS. 6a and 6b, in a language or dialect, a phoneme 400 (from the Greek: φώνημα, phōnēma, "a sound uttered") is the smallest segmental unit of sound employed to form meaningful contrasts between utterances. When an audio lesson 402 is played to a learner, the phoneme start/stop times 404 for each phoneme 400 are determined. The critical interval 406 around each phoneme includes the word containing the phoneme as well as morphosyntactic grammatical features that terminate in the word. EEG analysis is synchronized to the start of each phoneme 400 by applying a phoneme-locked window 408 to the continuous multi-channel EEG signals 410 starting at each phoneme. EEG analysis is assumed to pertain to the words that intersect with the critical interval 406 as well as grammatical traits (subject noun agreement, for example) that terminate in the critical interval. The output cues of the EEG analysis are correlated with the latent traits associated with the text in the critical interval 406. This process is suitably repeated for each and every phoneme.

The EEG classifier can, for example, be constructed to extract features (e.g. time domain such as amplitude, frequency domain such as power, spatial patterns or components such as via LCA) from one or more time windows and render a likelihood output (continuous value from 0 to 1) or decision output (binary value of 0 or 1) based on a weighted (linear or non-linear) combination of the features. Typical classifiers include the LDA, support vector machine (SVM), neural networks or AdaBoost. A rich set of features may be available from which a smaller subset of features are selected for a particular application based on training. The classifier is trained based on the extracted features to detect a significant brain response for a single-trial relevant stimulus. The classifier may be trained to recognize any significant brain response or, more typically, it may be trained to recognize significant brain response for particular relevant stimuli and reject significant brain responses for non-relevant stimuli.

The brain response to stimuli reflects neurophysiological activities located in selectively distributed sites of the brain evolving with a continuous time course. By locking EEG analysis to the stimulus, the classifier may be configured in many different ways. Each fixation-event or phoneme may be used as a marker to extract a broad window of data (e.g. 0-800 ms) that is presented to a single multi-channel spatial classifier. Independent Component Analysis (ICA) that tends to separate independent activity in the brain may be effective at separating the different ERPs. Common Spatial Subspace Decomposition, which is similar to ICA, models correlations in the spatial activations of the brain to provide addition discrimination. Alternately, a spatio-temporal classifier includes multiple spatial classifiers that correspond to different narrow windows having different offsets from the marker and a temporal classifier that detects temporal patterns in the outputs of the multiple spatial classifiers. The spatio-temporal classifier attempts to capture the spatio-temporal pattern that evolves as a cognitive brain response progresses through the brain in response to a relevant stimulus by collecting evidence of this non-stationary signal and combining it to improve detection confidence. For example, the spatial classifiers may roughly correspond to certain ERPs and the temporal classifier to temporal patterns of the ERPs. The classifier may be trained to not only output an overall cue representative of cognitive response but also to classify the various ERPs that cause the response. The classifier may be configured to output a cue (a binary decision or a likelihood) that a significant brain response has occurred.

Spatio-Temporal Classifier

Figure 7A:
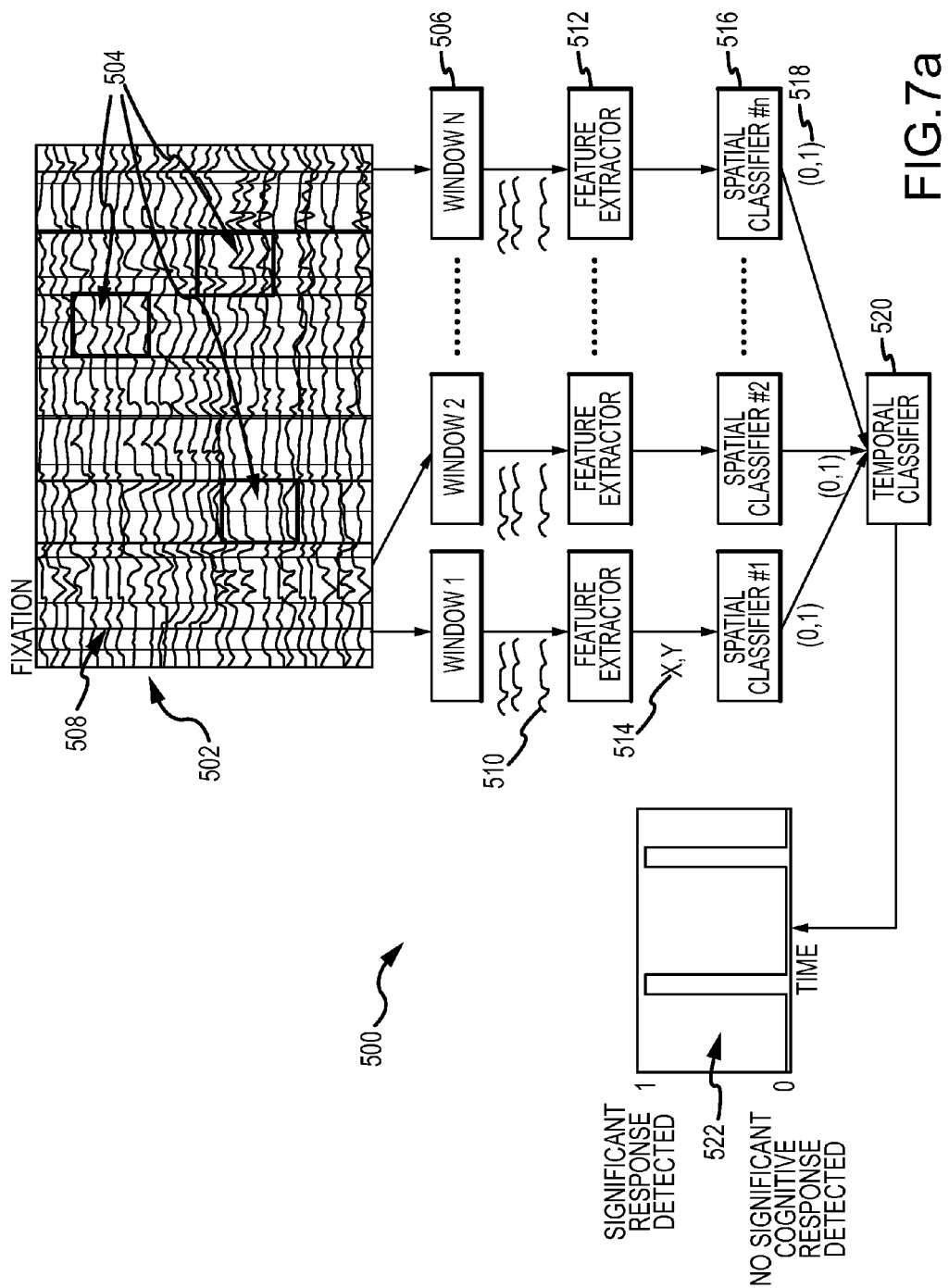
FIGS. 7a and 7b are a block diagram of an embodiment of a spatio-temporal classifier for processing the fixation or phoneme-locked EEG signals to generate the output cue and an embodiment of ERP specific temporal windows for segmenting the EEG signals.

Referring now to FIG. 7a, a spatio-temporal classifier 500 is configured as the post-fixation locked sub-classifier. The classifier is trained to detect significant brain responses for either visual or spoken text stimuli and generate the appropriate cue.

Electrodes on a learner's scalp generate multiple spatial channels of EEG data 502 in response to various stimuli. Each spatial channel includes a temporal signal 504 typically representative of an amplitude difference between a pair of electrodes. Unlike other methods of detecting brain responses such as MRI, EEG data has a very fine time resolution. To detect significant brain responses to task-relevant stimuli, we configure the classifier to capture the evolving spatio-temporal pattern as the response to the stimuli propagates through certain distributed areas of the brain. In general, the classifier is not classifying the stimulus itself but is deciding whether a significant brain-response has occurred. The classifier may be trained to detect any significant brain response or it may be trained to detect significant brain responses for certain types of task-relevant stimulus e.g. certain targets of interest in images. The classifier may be trained to classify different types or classes of stimulus.

The EEG data is subdivided into a plurality of windows 506 starting at the fixation event 508 (or phoneme) (t=0 ms) sufficient to capture the temporal evolution of the brain response to a pre or post-fixation stimulus (e.g. 700 ms).

Each window contains a different temporal segment of data 510 offset from the onset of fixation event 510 for a subset, typically all, of the spatial channels. In order to detect temporal patterns across the different time windows it is useful to control four separate parameters; the window duration, the number of windows, the total temporal window captured and the overlap between windows. The window duration and overlap are typically uniform but could be tailored based on specific training for certain applications. Window duration may be in the range of 20-200 ms and more typically 50-100 ms; long enough to capture signal content with sufficient SNR yet short enough to represent a distinct portion of the non-stationary signal. The number of windows must be sufficient to provide a robust temporal pattern. The total temporal window typically spans the onset of the stimuli to a threshold window beyond which the additional data does not improve results. The threshold may be assigned based on the response of each subject or based on group statistics. The threshold window for most subjects for our experimental stimuli is near 700 ms. Window overlap is typically 25-50%, sufficient to center critical brain response transitions within windows and to provide some degree of temporal correlation between spatial classifiers. Larger overlaps may induce too much correlation and become computationally burdensome. The number of windows, position and duration may be selected to correspond to particular ERPs. Knowledge of the environment, nature of the stimuli and the ERPs invoked by the stimuli may be used to optimize the classifier.

Feature extractors 512 extract features X, Y, ... 514 from the respective windows of EEG data. These features may be time-domain features such as amplitude, frequency-domain features such as power, spatial domain or independent components or combinations thereof. Features may include signal amplitude, absolute amplitude, short moving average, instantaneous power in a specific frequency range, etc. The extracted features may or may not be the same for each window. To optimize performance and/or reduce the computational load, the nature and number of features will be determined during classifier training, typically for a particular task-relevant application. For example, classifier training may reveal that certain features are better discriminators in early versus late windows. Furthermore, since the temporal evolution of the signal roughly corresponds to its propagation through different areas of the brain features may be extracted from different subsets of spatial channels for the different windows. Training would identify the most important spatial channels for each window.

In an embodiment, Independent Component Analysis is used to identify distinct features. A series of sentences (alternating audible and visual presentations) are presented to the learner in L1 (the reader's native language). These sentences are designed to evoke ELAN, LAN, N400 and P600 and can include syntactic and semantic errors as well as nonsense words. ICA is used to identify distinct components in EEG and associate these components with presumed sources (eye movements, semantic errors, phrase-structure errors, etc). The sentences are presented in the native language with no errors, syntactic errors, word order/phrase errors and semantic errors ("I brushed my hair with the stereo.") to elicit ELAN, LAN, N400 and P600 in the native language, as well as to elicit other EEG components (P300, etc) that may be relevant to assessing language understanding. The N400, P600, and other components are identified through association of the spatio-temporal ICA component with linguistic errors known to elicit that component.

Once extracted, the features from the different temporal windows are presented to respective spatial sub-classifiers 516. Each sub-classifier is trained based on the extracted features for its particular window to detect a significant brain response to a language-learning stimulus. Brain activity is measured and recorded for the myriad of learning-language skills (the latent traits) under conditions demonstrating master and difficulty of the skills and the sub-classifiers are trained to discriminate between the two states. Specific techniques for training different classifiers are well known in the art. A linear discrimination analysis (LDA) classifier of the type used in single-window RSVP systems was configured and trained for each of the N spatial classifiers. The LDA classifier described by Parra linearly combines the multiple spatial EEG channels to form an aggregate representation of the data. Other linear and non-linear classifiers such as support vector machines (SVM), neural networks or AdaBoost could also be employed. Different sub-classifiers may be used for the different windows. Each sub-classifier 516 generates a first level output 518. The sub-classifiers may be configured to generate either a likelihood output e.g. a continuous value from 0 to 1, or a decision output e.g. a binary value of 0 or 1 depending on the type of fusion used to combine the outputs.

The spatial sub-classifiers' first level outputs are presented to a temporal classifier 520 that combines them to detect temporal patterns across the different time windows relating to the evolution of the non-stationary brain response to task-relevant stimulus and to generate a second level output 522 indicative of the occurrence or absence of the significant non-stationary brain response. In this configuration, the second level output is a binary decision as to the brain state for a current stimulus. Although there is some latency due to data collection e.g. 500 ms from the onset of the fixation event, the processing time is small, approximately 5 ms, so that the system can generate decision level outputs in real-time that keep up with the presentation or occurrence of stimuli. Alternately, the second level output may be a continuous value form 0 to 1 indicative of the likelihood (e.g. 0-100%) of significant cognitive response.

Feature-level fusion detects the temporal pattern using a global classifier such as a LDA or a relevance vector machine (RVM). The continuous valued outputs of the spatial classifiers are considered as inputs features. For the LDA classifier, let y be the observed vector of spatial classifier output, a weight vector W can be derived based on training data to generate a one-dimension projection $z=W^T y$ where the dimension of the weight vector W is the number of spatial classifiers M. The projection z serves as an estimate of global pattern. The likelihood that a measurement belongs to the target class is assumed to follow a logistic distribution e.g. $p(H_1|y)=1/(1+e^{-z})$. Receiver operating characteristic (ROC) curves can be obtained by comparing $p(H_1|y)$ to a threshold $\eta$ having a value in [0,1]. The decision rule can be $p(H_1|y) \geq \eta$, out=1 and $p(H_1|y) \leq \eta$, out=0 or vice versa where out=1 represent a classifier's decision to declare detection of significant brain response and out=0 represents a classifier's decision to declare a non-significant brain response. When real data is presented to the temporal classifier, the weigh vector W will combine the outputs to discriminate patterns that indicate significant brain response from those that do not.

A RVM classifier models the likelihood that a measurement belongs to the target class as a sigmoid logistic function distribution $p(H_1|y)=1/(1+e^{-f_{RVM}(y)})$ where $f_{RVM}(y)=\Sigma(\alpha_i K(y,y_i)+b)$ for i=1 to M where $K(y,y_i)$ is the kernel function, $\alpha_i$ is the weight parameter for each spatial classifier output and b is a threshold. To determine the $\alpha_i$ using a Bayesian approach, they are encoded to have a sparse prior: statistically independent from each other and follow a zero-mean, Gaussian distribution with variance $\lambda_i^{-1}$; in addition, a gamma distribution is assumed on the hyper-parameter $\lambda_i$. Therefore, prior $\alpha_i$ are highly concentrated around 0 and generate very few nonzero terms in $f_{RVM}(y)$. A maximum a posteriori (MAP) estimate for the weight parameters $\alpha_i$ can be obtained by maximizing the posterior distribution of the class labels given the training set. The same decision rule can be applied.

Decision-level fusion detects temporal patterns by optimizing complementarities of the spatial sub-classifiers' binary decisions. Decision-level fusion is implemented to achieve an optimal combination of maximum likelihood estimates achievable between two or more alternative and complementary decisions. Training provides the operating points for the decision-level classifier.

An effective approach is to use Bayesian inference where spatial classifiers' binary decisions are treated as multiple hypotheses that need to be combined optimally. The hypotheses are $H_0$ (distractor) and $H_1$ (task-relevant stimulus). The spatial classifier output vector has joint probability density function $P(y_1, \ldots, y_k|H_j)$ under hypothesis $H_j$, for j=0, 1 and k=2, ..., M. For individual local amplitude-based classifiers, they receive as inputs the N-dimension observation vector x (amplitude) and make the decisions based on the LDA classifier outputs (given a fixed value of decision threshold). The decisions drawn from M individual spatial classifiers are denoted as $u_k$, where k=1, 2, ... M and $u_k=0$ if the spatial classifier k decides $H_0$ and $u_k=1$ if the spatial classifier k decides $H_1$. Individual classifier's decision $u_k$ depends only on the spatial classifiers' output vectors y.

$$u_k = \alpha(x_k) = \begin{cases} 0, & \text{spatial classifier } k \text{ decides } H_0 \\ 1, & \text{spatial classifier } k \text{ decides } H_1 \end{cases}$$

The performance characteristics of individual classifier k can be specified by $P(u_k|H_j)$, where $P(u_k=1|H_0)=P_{fk}=$the probability of false alarm and $P(u_k=1|H_1)=P_{dk}=$probability of detection.

The global decision fusion classifier receives the decisions of the individual spatial classifiers as its inputs. The decision at the fused level, $$u = \varphi(u_1, u_2, \ldots, u_k) = \begin{cases} 0, & \text{global decision } H_0 \\ 1, & \text{global decision } H_1 \end{cases}$$

Depends only on spatial decision, their probability of detection $P_{dk}$, probability of false alarm $P_{fk}$ and how complementary they are to each other. Since multiple spatial LDA classifiers base their decisions on EEG raw signals in different temporal windows, the simplest assumption is that these decisions are statistically independent.

As previously described, a learner's cognitive response to the presentation of language learning lessons may be characterized by the ERP or temporal sequence of ERPs that caused a positive response. Because certain ERPs, namely ELAN, LAN, N400 and P600 have been identified and the language learning skills that trigger them understood, classifying the ERP that generates the cue provides additional evidence to discriminate the source of difficulty.

Figure 7B:
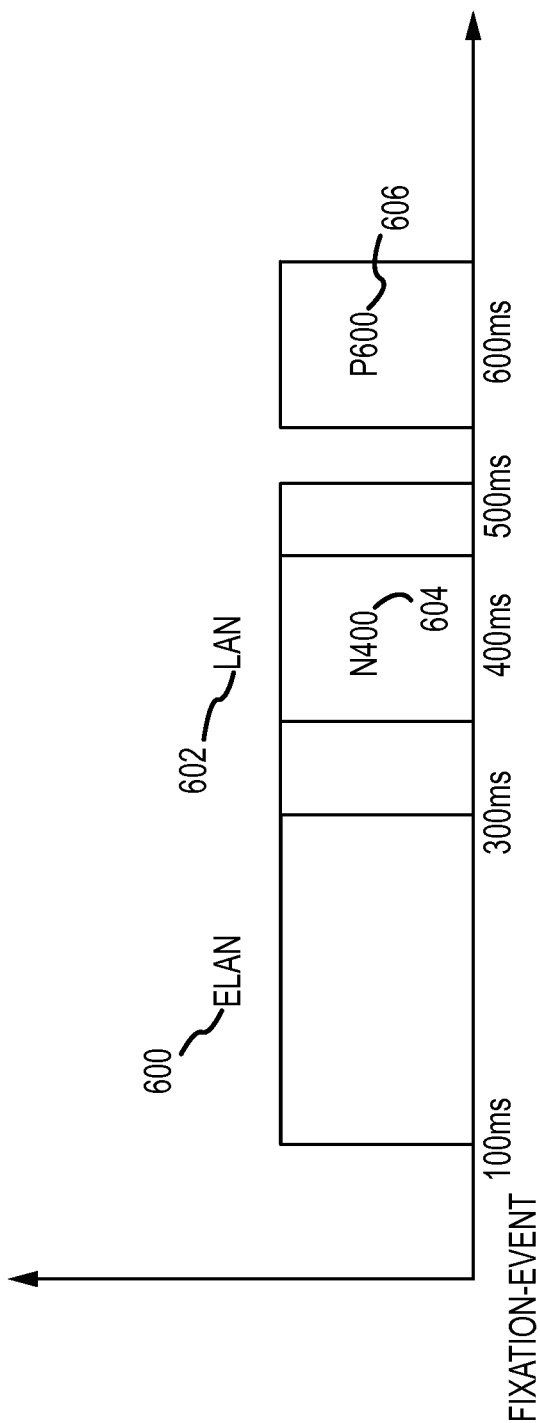

Referring now to FIGS. 7a and 7b, there are a number of ways the Classifier may be configured and trained to classify the ERPs. One approach would be to use multiple independent multi-channel spatial classifiers to classify different time segments of EEG data corresponding to the different ERPs. An ELAN window 600 might capture data from 100 to 300 ms after the fixation- or phoneme-event, a LAN window 602 might capture data from 300 to 500 ms after the event, an N400 window 604 might capture data from 350 to 450 ms, a P600 window 606 might capture data from 550 to 650 ms and so forth. The output of each classifier albeit a binary decision or likelihood value could be used for Bayesian update of the latent trait distributions. In another approach, these same windows could be used for the multi-channel spatial classifiers in the spatio-temporal classifier and the classifier trained to discriminate between ELAN, LAN, N400 and P600. The features extracted may also be selected to differentiate the various ERPs. The classifier would generate a single output cue with a label of the ERP or sequence of ERPs that generate the positive response. In a variation on this approach, the fusion classifier might generate one fused output and each of the ERP classifiers might generate their own ERP outputs. In yet another approach, the spatio-temporal classifier may use windows that are not specifically configured for the various ERP yet the classifier is trained to discriminate between ELAN, LAN, N400 and P600.

Figure 8A:
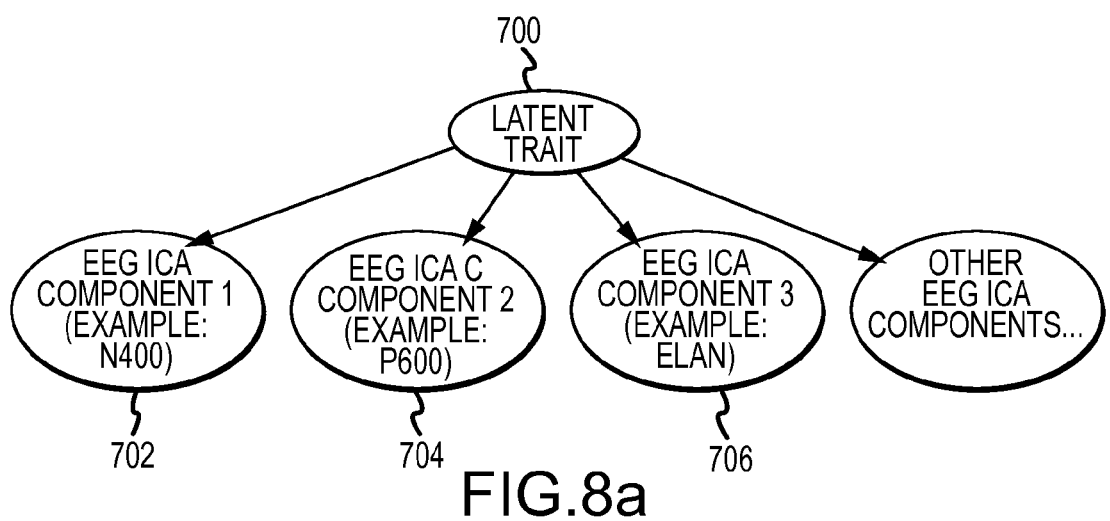
FIGS. 8a and 8b are diagrams of a Bayesian-network model for a single latent trait or multiple latent traits tested by each fixation or phoneme, respectively.
Figure 8B:
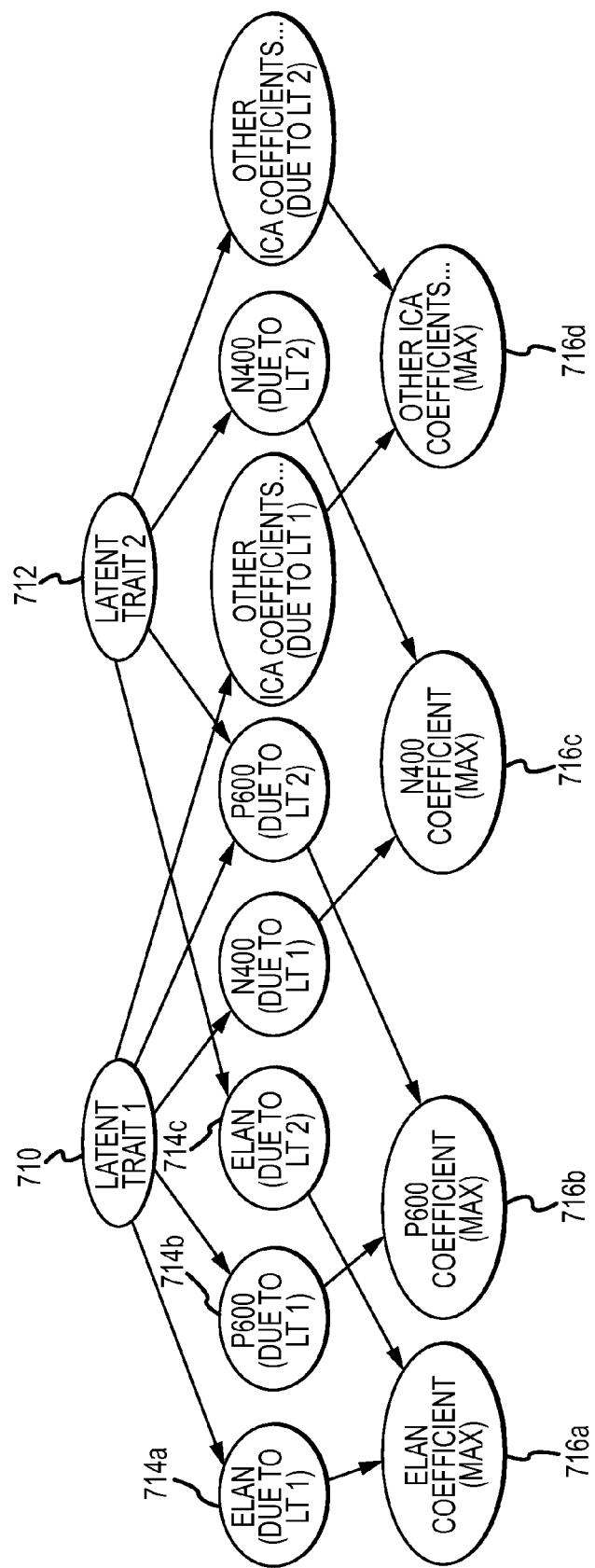

Referring now to FIGS. 8a and 8b, a single latent trait 700 may be characterized by multiple probability distributions for the respective ERPs; N400 702, P600 704, ELAN 706 and so forth instead of just a single distribution for cognitive response. The latent trait will also be characterized by distributions for the learner's motor response, saccades and fixation duration. The value of this is if the classifier generates a cue for N400 this provides more evidence to discriminate the latent trait than would a cue for a cognitive response.

Often the language learning materials associated with each fixation-event or phoneme will test multiple traits 710 712 as shown in FIG. 8b. For example, if the tested latent traits are word familiarity, phrase structure and grammar features and output cue is classified as N400 than it is much more likely that the latent trait that caused the response was a difficulty with word familiarity. Similarly if the output cue was classified as ELAN it is much more likely that difficulty with phrase structure caused the response. Of course the latent traits are not perfectly separable, each will have a corresponding probability distribution 714a, 714b, 714c and so forth for each of the ERPs. Thus if a certain ERP is observed it may have been caused by more than one of the latent traits. Under the "noisy max" approach the Bayesian network assumes that the measured EEG component 716a, 716b, 716c and 716d is the maximum of the coefficients for the individual latent traits. Thus by knowing the output of the classifier for a particular ERP the Bayesian network can infer which of the latent traits was likely to have caused the positive response.

The classification of each stimulus-locked response and the inference of which latent trait caused the response is a complex statistical process. The ability to classify the learner's cognitive response to each stimulus and to correlate that to a limited set of latent traits greatly increases the information available to identify the source of language learning difficulty. However, the value of such a process does not lie in a single measurement or even a small number of measurements. The value lies in assessing each and every stimulus-locked event (fixation or phoneme) and continuously updating the model as the learner progresses through the lessons.

A bibliography of references cited herein is listed below:

Pierre Comon (1994). "Independent component analysis, A new concept?" Signal Processing 36.

Frenck-Mestre, C. (2005). "Eye-movement recording as a tool for studying syntactic processing in a second language: A review of methodologies and experimental findings." Second Language Research.

Angela Friederici, Jürgen Weissenborn (2007). "Mapping sentence form onto meaning: The syntax-semantic interface. Brain Research 1146: 52.A. Hahne (2001). What's different in second-language processing?" Evidence from event-related brain potentials. Journal of Psycholinguistic Research 2001, 30:251-266.

David Heckerman, John S. Breese (1995). "Causal Independence for Probability Assessment and Inference Using Bayesian Networks." IEEE Transactions on Systems, Man and Cybernetics.

Albrecht Inhoff, Seth Greenberg, Matthew Solomon and Chin-An Wang (2009). "Word integration and regression programming during reading: a test of the E-Z reader 10 model." Journal of Experimental Psychology: Human Perception and Performance Vol 35(5), October 2009, 1571-1584.

Taiichiro Ishida and Mitsuo Ikeda (1989). "Temporal properties of information extraction in reading studied by a text-mask replacement technique." JOSA A, Vol. 6, Issue 10, pp. 1624-1632.

Scott Makeig, Anthony Bell, Tzyy-Ping Jung, Terrence Sejnowski (1996). "Independent Component Analysis of Electroencephalographic Data." Advances in Neural Information Processing Systems 8, MIT Press, Cambridge Mass., 1996.

Jutta Mueller, Regine Oberecker and Angela Friederici (2009). "Syntatic learning by mere exposure: An ERP study in adult learners." BMC Neuroscience. 29 Jul. 2009.

Lee Osterhout; J. McLaughlin, I. Pitkanen, C. Frenck-Mestre, and N. Molinaro (2006). "Novice learners, longitudinal designs, and event-related potentials: A means for exploring the neurocognition of second language processing." Language Learning 2006, 56 (Suppl I): 199-230.

Keith Rayner (1998). "Eye movements in reading and information processing: 20 years of research." Psychological Bulletin. Vol 124(3), November 1998. 272-422.

Reichle, E. D.; A. Pollasek; K. Rayner (2006). "E-Z Reader: A cognitive-control, serial-attention model of eye-movement behavior during reading." Cognitive Science. 7: 4-22.

S. Rossi, M F Gugler, A D Friederici, A. Hahne (1996). "The impact of proficiency on syntactic second-language processing of German and Italian: Evidence from event-related potentials." Journal of Cognitive Neuroscience 1996, 8(3):231-256.

Kirsten Weber and Aureliu Lavric (2008). "Syntatic anomaly elicits a lexico-semantic (N400) ERP effect in the second language but not the first." Psychophysiology 45 (2008).

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A method of second language learning, comprising:
a) providing a user model of latent traits that represent different semantic and syntactic second language learning skills including word meanings and grammatical structures, a state of each said latent trait representing the learner's mastery of that second language learning skill;
b) presenting a lesson of second language learning materials including error-free text, text that includes syntax errors and text that includes semantic errors to test the one or more latent traits on a display to elicit a response from a learner, said materials presented on the display so that the learner is allowed to move his or her eyes freely in response to the displayed materials;
c) measuring EEG data of the learner's brain activity from a plurality of electrodes placed on the learner's scalp;
d) tracking the learner's eye movements to determine fixations on the materials; for each fixation,
e) locking a window to the fixation and applying that fixation-locked window to the EEG data to generate a time segment of EEG data;
f) extracting one or more features from the time segment of EEG data;
g) presenting said one or more features to a classifier to detect an event-related potential (ERP) to generate a fixation-locked cue indicative of whether the learner exhibited a significant cognitive response to the displayed materials;
h) identifying the text in the second language learning materials associated with the fixation;
i) retrieving from the user model the one or more latent traits tested by the identified text including the one or more words at the point of fixation and the grammatical structure that contains the one or more words;
j) using the fixation-locked cue to update the state of the one or more latent traits retrieved from the user model;
k) monitoring the states of the latent traits to assess mastery or difficulty the learner is having with specific learning skills; and
l) customizing a subsequent lesson based on the states of one or more latent traits in the user model.

2. The method of claim 1, wherein the user model is incrementally updated for each said fixation event throughout the presentation of the second language learning skills.

3. The method of claim 1, wherein the second language learning materials pose a question, further comprising:
recording a typed or auditory response by the learner to the question;
retrieving from the user model one or more latent traits tested by the question; and assessing the response to update the state of the one or more latent traits in the model.

4. The method of claim 1, further comprising:
presenting a lesson of second language learning materials via audio to elicit a response from the learner, said materials including phonemes that test one or more latent traits;
for a phoneme in the audio materials, applying a phoneme-locked window to the EEG data to generate a time segment of EEG data; and
repeating steps f through j to update the user model.

5. The method of claim 1, further comprising:
measuring a saccade between fixations; and
using the saccade to update the state of one or more latent traits associated with the fixation.

6. A method of second language learning comprising:
a) providing a user model of latent traits that represent different semantic and syntactic second language learning skills including word meanings and grammatical structures, a state of each said latent trait representing the learner's mastery of that second language learning skill, wherein the user model includes a probability distribution for the current state for each latent trait and a presentation history for each latent trait, said probability distribution weighted by a forgetting curve based on the presentation history;
b) presenting a lesson of second language learning materials including error-free text, text that includes syntax errors and text that includes semantic errors to test the one or more latent traits on a display to elicit a response from a learner, said materials presented on the display so that the learner is allowed to move his or her eyes freely in response to the displayed materials;
c) measuring EEG data of the learner's brain activity from a plurality of electrodes placed on the learner's scalp;
d) tracking the learner's eye movements to determine fixations on the materials; for each fixation,
e) locking a window to the fixation and applying a that fixation-locked window to the EEG data to generate a time segment of EEG data;
f) extracting one or more features from the time segment of EEG data;
g) presenting said one or more features to a classifier to detect an event-related potential (ERP) to generate a fixation-locked cue indicative of whether the learner exhibited a significant cognitive response to the displayed materials;
h) identifying the text in the second language learning materials associated with the fixation;
i) retrieving from the user model the one or more latent traits tested by the identified text including the one or more words at the point of fixation and the grammatical structure that contains the one or more words; and
j) using the fixation-locked cue to update the state of the one or more latent traits retrieved from the user model.

7. The method of claim 6, wherein a Bayesian network is used to update the probability distributions based on the fixation-locked cue.

8. The method of claim 1, where steps (f) and (g), comprise:
subdividing the time segment of EEG data into a plurality of time sub-segments each with a different offset to the fixation;
separately extracting features from each said time sub-segment of EEG data;
presenting the extracted features to a respective plurality of spatial sub-classifiers trained to detect spatial patterns of said extracted features during different time segments after the fixation and to generate first level outputs indicative of the occurrence or absence of a significant cognitive response; and
presenting the plurality of spatial sub-classifier first level outputs to a temporal classifier to detect temporal patterns across the different time sub-segments relating to the evolution of the non-stationary brain response to task-relevant stimulus and to generate a second level output as the fixation-locked cue indicative of the occurrence or absence of the significant non-stationary cognitive response.

9. The method of claim 8, wherein the presented text is designed to evoke ELAN, LAN, N400 and P600 ERPs, wherein each said spatial sub-classifier is trained to classify and output a different one of the ELAN, LAN, N400 and P600 ERPs.

10. The method of claim 9, wherein the fixation-locked cue is labeled with the specific ERP or sequence of ERPs that generate the positive response.

11. The method of claim 9, wherein the time segment of EEG data is subdivided into an ELAN time-segment that spans approximately 100 to 300 ms, a LAN time-segment that spans approximately 300 to 500 ms, an N400 window that spans approximately 350 to 450 ms and a P600 window that spans approximately 440 to 650 ms.

12. The method of claim 9, wherein the fixation-locked cue is labeled with the temporal output and the ERP output from each spatial classifier.

13. A method of second language learning, comprising:
a) providing a user model of latent traits that represent different semantic and syntactic second language learning skills including word meanings and grammatical structures, a state of each said latent trait representing the learner's mastery of that second language learning skill;
b) presenting lessons of second language learning materials including visual materials on a display and audio materials via an audio speaker or headphones to elicit a response from a learner, said materials including error-free text, text that includes syntax errors and text that includes semantic errors to test the one or more latent traits, said visual materials presented on the display so that the learner is allowed to move his or her eyes freely in response to the displayed materials;
c) measuring EEG data of the learner's brain activity from a plurality of electrodes placed on the learner's scalp;
d) tracking the learner's eye movements to provide position signals;
e) processing the position signals to determine fixations on the visual materials;
f) determining phonemes in the presented audio materials;
g) applying a stimulus-locked window to the EEG data at each fixation or phoneme to generate a sequence of time segments of EEG data;
h) extracting one or more features from each said time segment of EEG data;
i) presenting said one or more features to a classifier to generate a stimulus-locked cue indicative of whether the learner exhibited a significant cognitive response in the form of an event-related potential (ERP) to the materials;
j) identifying the second language learning materials associated with each fixation or phoneme;
k) computing a saccade or fixation duration metric from the position signals;

l) retrieving from the user model the one or more latent traits tested by the second language learning materials associated with the fixation;

m) using the stimulus-locked cue and saccade or fixation duration metric to update the state of the one or more latent traits retrieved from the user model for each fixation and phoneme;

n) monitoring the states of the latent traits to assess mastery or difficulty the learner is having with specific learning skills; and o) customizing a subsequent lesson based on the states of one or more latent traits in the user model.

14. The method of claim 13, wherein the second language learning materials pose a question, further comprising:

recording a typed or auditory response by the learner to the question;

retrieving from the user model one or more latent traits tested by the question; and assessing the response to update the state of the one or more latent traits in the model.

15. The method of claim 13, wherein the classifier labels the fixation-locked cue with one of a plurality of ERPs including ELAN, LAN, N400 and P600 that generated the cue.

16. A method of second language learning, comprising:

providing a user model of latent traits that represent different semantic and syntactic second language learning skills including word meanings and grammatical structures, a state of each said latent trait representing the learner's mastery of that second language learning skill;

presenting second language-learning materials including error-free text, text that includes syntax errors and text that includes semantic errors to test the one or more latent traits on a display so that a learner is allowed to move his or her eyes freely in response to the displayed materials;

measuring EEG data of the learner's brain activity from a plurality of electrodes placed on the learner's scalp;

tracking the learner's eye movement to determine fixation events on the materials;

at each fixation event, processing a time window of EEG data to identify a fixation-locked cognitive response in the form of an event-related potential (ERP);

associating each fixation-locked cognitive response with a portion of the displayed materials;

processing each said fixation-locked cognitive response and the associated materials to update the state of the one or more latent traits tested by those materials;

monitoring the states of the latent traits to assess mastery or difficulty the learner is having with specific learning skills; and customizing a subsequent lesson based on the states of one or more latent traits in the user model.

17. The method of claim 16, wherein the second language learning materials pose a question, further comprising:

recording a typed or auditory response by the learner to the question; and processing the typed or auditory response and the cognitive response with the materials to update the state of the one or more latent traits tested by those materials.

18. The method of claim 16, further comprising:

measuring a saccade from the eye movement; and processing the saccade and the cognitive response with the materials to update the state of the one or more latent traits tested by those materials.

19. The method of claim 16, wherein the fixation-locked cognitive response is labeled with one of a plurality of event-related potentials (ERPs) that generated the response.

20. A method of second language learning, comprising:

a) providing a user model of latent traits that represent different semantic and syntactic second language learning skills including word meanings and grammatical structures, a state of each said latent trait representing the learner's mastery of that second language learning skill;

b) presenting a lesson of second language learning materials including error-free text, text that includes syntax errors and text that includes semantic errors to test the one or more latent traits on a display to elicit a response from a learner, said materials designed to evoke ELAN, LAN, N400 and P600 event-related potentials (ERPs) in the learner, said materials presented on the display so that the learner is allowed to move his or her eyes freely in response to the displayed materials;

c) measuring EEG data of the learner's brain activity from a plurality of electrodes placed on the learner's scalp;

d) tracking the learner's eye movements determine a sequence of fixations on the materials; for each fixation, e) locking a window to the fixation and applying that fixation-locked window to the EEG data to generate a time segment of EEG data that captures an evolving temporal signature in response to the fixation;

f) extracting one or more features from the time segment of EEG data;

g) presenting said one or more features to a single-trial classifier to detect ELAN, LAN, N400 and P600 ERPs to generate a fixation-locked cue indicative;

h) synchronizing the fixation-locked cue to a specific phrase in the second language learning materials;

i) retrieving from the user model the one or more latent traits tested by the specific phrase synchronized to the fixation-locked cue;

j) using the fixation-locked cue to update the state of the one or more latent traits retrieved from the user model k) monitoring the states of the latent traits to assess mastery or difficulty the learner is having with specific learning skills; and l) customizing a subsequent lesson based on the states of one or more latent traits in the user model.

* * * * *